US009758600B1

(12) United States Patent
Praetorius et al.

(10) Patent No.: US 9,758,600 B1
(45) Date of Patent: Sep. 12, 2017

(54) BICYCLIC BRIDGED METALLOCENE COMPOUNDS AND POLYMERS PRODUCED THEREFROM

(71) Applicant: Chevron Phillips Chemical Company LP, The Woodlands, TX (US)

(72) Inventors: Jeremy M. Praetorius, Bartlesville, OK (US); Qing Yang, Bartlesville, OK (US); Connor D. Boxell, Bartlesville, OK (US); Tony R. Crain, Niotaze, KS (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/465,643

(22) Filed: Mar. 22, 2017

Related U.S. Application Data

(63) Continuation-in-part of application No. 15/163,730, filed on May 25, 2016.

(51) Int. Cl.
  *C08F 4/6592* (2006.01)
  *C07F 17/00* (2006.01)

(52) U.S. Cl.
  CPC .......... *C08F 4/65927* (2013.01); *C07F 17/00* (2013.01)

(58) Field of Classification Search
  CPC .............................. C07F 17/00; C08F 4/65927
  See application file for complete search history.

(56) References Cited

U.S. PATENT DOCUMENTS

| | | | |
|---|---|---|---|
| 3,242,099 A | 3/1966 | Manyik et al. | |
| 3,248,179 A | 4/1966 | Norwood | |
| 4,501,885 A | 2/1985 | Sherk et al. | |
| 4,588,790 A | 5/1986 | Jenkins, III et al. | |
| 4,794,096 A | 12/1988 | Ewen | |
| 4,808,561 A | 2/1989 | Welborn, Jr. | |
| 5,352,749 A | 10/1994 | DeChellis et al. | |
| 5,436,304 A | 7/1995 | Griffin et al. | |
| 5,565,175 A | 10/1996 | Hottovy et al. | |
| 5,575,979 A | 11/1996 | Hanson | |
| 5,576,259 A | 11/1996 | Hasegawa et al. | |
| 5,739,220 A | 4/1998 | Shamshoum et al. | |
| 5,807,938 A | 9/1998 | Kaneko et al. | |
| 5,919,983 A | 7/1999 | Rosen et al. | |
| 6,107,230 A | 8/2000 | McDaniel et al. | |
| 6,153,549 A | 11/2000 | Hübscher et al. | |
| 6,165,929 A | 12/2000 | McDaniel et al. | |
| 6,239,235 B1 | 5/2001 | Hottovy et al. | |
| 6,262,191 B1 | 7/2001 | Hottovy et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,339,134 B1* | 1/2002 | Crowther ............. B01J 31/1608 | |
| | | | 502/152 |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 6,833,415 B2 | 12/2004 | Kendrick et al. | |
| 6,875,719 B2 | 4/2005 | Tsai et al. | |
| 6,930,157 B2 | 8/2005 | Tsai et al. | |
| 7,026,494 B1 | 4/2006 | Yang et al. | |
| 7,294,599 B2 | 11/2007 | Jensen et al. | |
| 7,468,452 B1 | 12/2008 | Martin et al. | |
| 7,531,606 B2 | 5/2009 | Hendrickson | |
| 7,598,327 B2 | 10/2009 | Shaw | |
| 7,601,665 B2 | 10/2009 | McDaniel et al. | |
| 7,884,163 B2 | 2/2011 | McDaniel et al. | |
| 7,956,139 B2 | 6/2011 | Yang et al. | |
| 8,114,946 B2 | 2/2012 | Yang et al. | |
| 8,222,174 B2 | 7/2012 | Yang et al. | |
| 8,309,485 B2 | 11/2012 | Yang et al. | |
| 8,309,747 B2 | 11/2012 | Yang et al. | |
| 8,623,973 B1 | 1/2014 | McDaniel et al. | |
| 8,703,886 B1 | 4/2014 | Yang et al. | |
| 8,822,608 B1 | 9/2014 | Bhandarkar et al. | |
| 9,023,959 B2 | 5/2015 | McDaniel et al. | |
| 9,102,768 B2 | 8/2015 | Praetorius et al. | |
| 9,102,798 B2 | 8/2015 | Weber et al. | |
| 9,359,460 B2 | 6/2016 | Praetorius et al. | |
| 2004/0059070 A1 | 3/2004 | Whitte et al. | |
| 2014/0343238 A1* | 11/2014 | Al-Humydi ............. C07F 17/00 | |
| | | | 526/170 |
| 2016/0208025 A1* | 7/2016 | Sankaran ............. C08F 110/02 | |

FOREIGN PATENT DOCUMENTS

WO  WO 2015/028595  3/2015

OTHER PUBLICATIONS

Modem Plastics Encyclopedia, Mid-Nov. 1995 Issue, vol. 72, No. 12, 3 pages.
Film Extrusion Manual—Process, Materials, Properties, TAPPI Press, 1992, 16 pages.
U.S. Appl. No. 15/163,730, filed May 25, 2016 entitled "Bicyclic Bridged Metallocene Compounds and Polymers Produced Therefrom."

* cited by examiner

*Primary Examiner* — Caixia Lu
(74) *Attorney, Agent, or Firm* — Merchant & Gould P.C.

(57) ABSTRACT

Disclosed herein are catalyst compositions containing bicyclic bridged metallocene compounds. These catalyst compositions can be used for the polymerization of olefins. For example, ethylene polymers produced using these catalyst compositions can be characterized by low molecular weights and high melt flow rates, and can be produced without the addition of hydrogen.

20 Claims, 9 Drawing Sheets

BICYCLIC BRIDGED METALLOCENE COMPOUNDS AND POLYMERS PRODUCED THEREFROM

REFERENCE TO RELATED APPLICATION

This application is a continuation-in-part application of co-pending U.S. patent application Ser. No. 15/163,730, filed on May 25, 2016, the disclosure of which is incorporated herein by reference in its entirety.

BACKGROUND OF THE INVENTION

Polyolefins such as high density polyethylene (HDPE) homopolymer and linear low density polyethylene (LLDPE) copolymer can be produced using various combinations of catalyst systems and polymerization processes. In some end-use applications, it can be beneficial for the catalyst system employed to produce low molecular weight and high melt flow polymers without the use of hydrogen. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention generally relates to new catalyst compositions, methods for preparing the catalyst compositions, methods for using the catalyst compositions to polymerize olefins, the polymer resins produced using such catalyst compositions, and articles produced using these polymer resins. In particular, the present invention relates to bicyclic bridged metallocene compounds, and to catalyst compositions employing such metallocene compounds. Catalyst compositions of the present invention that contain these bicyclic bridged metallocene compounds can be used to produce, for example, ethylene-based homopolymers and copolymers.

In accordance with an aspect of the present invention, disclosed and described herein are bicyclic bridged metallocene compounds having the formula:

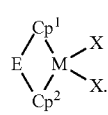

(B)

In formula (B), M can be Ti, Zr, or Hf; each X independently can be any monoanionic ligand disclosed herein; $Cp^1$ and $Cp^2$ independently can be a cyclopentadienyl, indenyl, or fluorenyl group, optionally substituted with any substituent disclosed herein; and E can be any bicyclic bridging group disclosed herein.

Catalyst compositions containing the bicyclic bridged metallocene compounds of formula (B) also are provided by the present invention. In one aspect, a catalyst composition is disclosed which comprises a bicyclic bridged metallocene compound of formula (B) and an activator. Optionally, this catalyst composition can further comprise a co-catalyst, such as an organoaluminum compound. In some aspects, the activator can comprise an activator-support, while in other aspects, the activator can comprise an aluminoxane compound, an organoboron or organoborate compound, an ionizing ionic compound, or combinations thereof.

The present invention also contemplates and encompasses olefin polymerization processes. Such processes can comprise contacting a catalyst composition with an olefin monomer and optionally an olefin comonomer in a polymerization reactor system under polymerization conditions to produce an olefin polymer. Generally, the catalyst composition employed can comprise any of the bicyclic bridged metallocene compounds disclosed herein and any of the activators disclosed herein. Further, organoaluminum compounds or other co-catalysts also can be utilized in the catalyst compositions and/or polymerization processes.

Polymers produced from the polymerization of olefins, resulting in homopolymers, copolymers, terpolymers, etc., can be used to produce various articles of manufacture. A representative and non-limiting example of an olefin polymer—in this case, an ethylene homopolymer or ethylene/α-olefin copolymer (e.g., an ethylene/1-butene copolymer, an ethylene/1-hexene copolymer, or an ethylene/1-octene copolymer)—consistent with aspects of this invention can be characterized by the following properties: a melt index in a range from about 250 to about 2000 g/10 min (or from about 400 to about 1000 g/10 min, or greater than 500 g/10 min), and/or a density in a range from about 0.87 to about 0.96 g/cm³ (or from about 0.89 to about 0.93 g/cm³), and/or a Mw in a range from about 10,000 to about 25,000 g/mol (or from about 12,000 to about 23,000 g/mol), and/or an Mn in a range from about 3,000 to about 13,000 g/mol (or from about 4,500 to about 10,000 g/mol), and/or a ratio of Mw/Mn in a range from about 2 to about 3.5 (or from about 2 to about 2.5).

Another representative and non-limiting example of an olefin polymer—in this case, an ethylene homopolymer or ethylene/α-olefin copolymer (e.g., an ethylene/1-butene copolymer, an ethylene/1-hexene copolymer, or an ethylene/1-octene copolymer)—consistent with aspects of this invention can be characterized by the following properties: a melt index in a range from about 10 to about 200 g/10 min (or from about 20 to about 150 g/10 min), and/or a density in a range from about 0.87 to about 0.96 g/cm³ (or from about 0.89 to about 0.93 g/cm³), and/or a Mw in a range from about 27,000 to about 65,000 g/mol (or from about 30,000 to about 60,000 g/mol), and/or an Mn in a range from about 12,000 to about 35,000 g/mol (or from about 14,000 to about 30,000 g/mol), and/or a ratio of Mw/Mn in a range from about 2 to about 3.5 (or from about 2 to about 2.5).

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

DEFINITIONS

Figure 1:
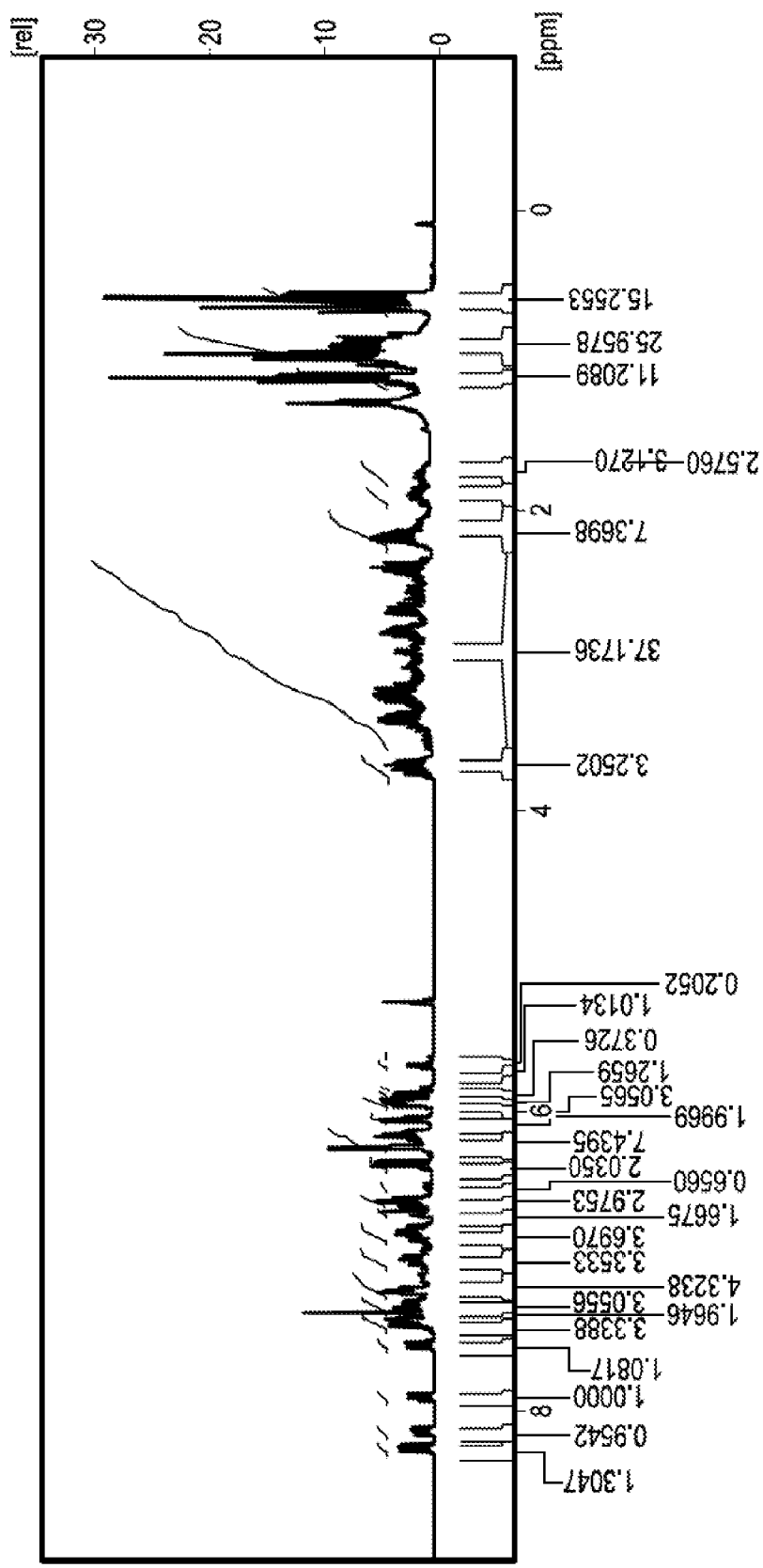
FIG. 1 presents a ¹H-NMR plot of the Metallocene M1-(NEt₂)₂ isomer mixture of Example 1.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the compounds, compositions, processes, or methods described herein are contemplated with or without explicit description of the particular combination. Additionally, unless explicitly recited otherwise, any aspect or feature disclosed herein can be combined to describe inventive compounds, compositions, processes, or methods consistent with the present disclosure.

While compositions and methods are described herein in terms of "comprising" various components or steps, the compositions and methods can also "consist essentially of" or "consist of" the various components or steps, unless stated otherwise. For example, a catalyst composition consistent with aspects of the present invention can comprise; alternatively, can consist essentially of; or alternatively, can consist of; a bicyclic bridged metallocene compound, an activator, and optionally, a co-catalyst.

The terms "a," "an," "the," etc., are intended to include plural alternatives, e.g., at least one, unless otherwise specified. For instance, the disclosure of "an activator-support" or "a metallocene compound" is meant to encompass one, or mixtures or combinations of more than one, activator-support or metallocene compound, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any compound(s) disclosed herein, the structure or name presented is also intended to encompass all structural isomers, conformational isomers, and stereoisomers that can arise from a particular set of substituents, or the binding of different enantiotopic faces of a cyclopentadienyl-type ligand (e.g., substituted cyclopentadienyl, indenyl, substituted fluorenyl, etc.) to a metal atom, unless indicated otherwise. Thus, a general reference to a compound includes all structural isomers unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general or specific structure or name encompasses all enantiomers, diastereomers, and other optical isomers whether in enantiomeric or racemic forms, as well as mixtures of stereoisomers, as the context permits or requires.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

The term "polymer" is used herein generically to include olefin homopolymers, copolymers, terpolymers, and so forth, as well as alloys and blends thereof. The term "polymer" also includes all possible geometrical configurations, unless stated otherwise, and such configurations can include isotactic, syndiotactic, and random symmetries. The term "polymer" also includes impact, block, graft, random, and alternating copolymers. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer can be categorized an as ethylene/1-hexene copolymer.

In like manner, the scope of the term "polymerization" includes homopolymerization, copolymerization, terpolymerization, etc. Therefore, a copolymerization process can involve contacting one olefin monomer (e.g., ethylene) and one olefin comonomer (e.g., 1-hexene) to produce a copolymer.

The term "co-catalyst" is used generally herein to refer to compounds such as aluminoxane compounds, organoboron or organoborate compounds, ionizing ionic compounds, organoaluminum compounds, organozinc compounds, organomagnesium compounds, organolithium compounds, and the like, that can constitute one component of a catalyst composition, when used, for example, in addition to an activator-support. The term "co-catalyst" is used regardless of the actual function of the compound or any chemical mechanism by which the compound may operate.

The term "activator-support" is used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the activator-support can comprise a calcined contact product of at least one solid oxide with at least one electron-withdrawing anion source compound. The terms "support" and "activator-support" are not used to imply these components are inert, and such components should not be construed as an inert component of the catalyst composition. The term "activator," as used herein, refers generally to a substance that is capable of converting a metallocene component into a catalyst that can polymerize olefins, or converting a contact product of a metallocene component and a component that provides an activatable ligand (e.g., an alkyl, a hydride) to the metallocene, when the metallocene compound does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The term "metallocene" as used herein describes compounds comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands can include H, therefore this invention comprises ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. In some contexts, the metallocene can be referred to simply as the "catalyst," in much the same way the term "co-catalyst" can be used herein to refer to, for example, an organoaluminum compound.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the co-catalyst, the metallocene compound, or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "contact product" is used herein to describe methods and compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the methods and compositions described herein. Combining additional materials or components can be done by any suitable method. This term encompasses mixtures, blends, solutions, slurries, reaction products, and the like, as well as combinations thereof. Although "contact product" can include reaction products, it is not required for the respective components to react with one another. Similarly, the term "contacting" is used herein to refer to materials which can be blended, mixed, slurried, dissolved, reacted, treated, or otherwise contacted in some other manner.

The terms Mn, Mw, and Mz, as used herein, are defined as follows: Mn: number-average molecular weight; Mw: weight-average molecular weight; and Mz: z-average molecular weight. These values are determined by calculations on the basis of molecular weight distribution curves determined using gel permeation chromatography (GPC), also known as size-exclusion chromatography (SEC).

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the ratio of Mw/Mn of an ethylene polymer consistent with aspects of this invention. By a disclosure that the ratio of Mw/Mn can be in a range from about 2 to about 3.5, the intent is to recite that the ratio of Mw/Mn can be any ratio in the range and, for example, can be equal to about 2, about 2.2, about 2.4, about 2.6, about 2.8, about 3, about 3.2, about 3.4, or about 3.5. Additionally, the ratio of Mw/Mn can be within any range from about 2 to about 3.5 (for example, from about 2 to about 2.8), and this also includes any combination of ranges between about 2 and about 3.5 (for example, the Mw/Mn ratio can be in a range from about 2 to about 2.5, or from about 3 to about 3.4). Likewise, all other ranges disclosed herein should be interpreted in a manner similar to these examples.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

DETAILED DESCRIPTION OF THE INVENTION

The present invention is directed generally to new catalyst compositions, methods for preparing the catalyst compositions, methods for using the catalyst compositions to polymerize olefins, the polymer resins produced using such catalyst compositions, and articles produced using these polymer resins. In particular, the present invention relates to bicyclic bridged metallocene complexes, to catalyst compositions employing these metallocene complexes, to polymerization processes utilizing such catalyst compositions, and to the resulting olefin polymers produced from the polymerization processes.

Bicyclic Bridged Metallocenes

Disclosed herein are novel bicyclic bridged metallocene compounds and methods of making these compounds. The bicyclic bridged metallocene compounds can contain any combination of cyclopentadienyl groups, indenyl groups, and fluorenyl groups. For instance, the metallocene compounds can have the following formula:

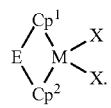

(B)

Within formula (B), M, E, $Cp^1$, $Cp^2$, and each X are independent elements of the metallocene compound. Accordingly, the metallocene compound having formula (B) can be described using any combination of M, E, $Cp^1$, $Cp^2$, and X disclosed herein.

Unless otherwise specified, formula (B) above, any other structural formulas disclosed herein, and any metallocene complex, compound, or species disclosed herein are not designed to show stereochemistry or isomeric positioning of the different moieties (e.g., these formulas are not intended to display rac or meso isomers, or R or S diastereoisomers), although such compounds are contemplated and encompassed by these formulas and/or structures, unless stated otherwise.

In accordance with aspects of this invention, the metal in formula (B), M, can be Ti, Zr, or Hf. In one aspect, for instance, M can be Ti or Zr, while in another aspect, M can be Ti; alternatively, M can be Zr; or alternatively, M can be Hf.

Each X in formula (B) independently can be a monoanionic ligand. In some aspects, suitable monoanionic ligands can include, but are not limited to, H (hydride), $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $-OBR^1_2$, or $-OSO_2R^1$, wherein $R^1$ is a $C_1$ to $C_{36}$ hydrocarbyl group. It is contemplated that each X can be either the same or a different monoanionic ligand.

In one aspect, each X independently can be H, $BH_4$, a halide (e.g., F, Cl, Br, etc.), a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group. Alternatively, each X independently can be H, $BH_4$, a halide, $OBR^1_2$, or $OSO_2R^1$, wherein $R^1$ is a $C_1$ to $C_{18}$ hydrocarbyl group. In another aspect, each X independently can be H, $BH_4$, a halide, a $C_1$ to $C_{12}$ hydrocarbyl group, a $C_1$ to $C_{12}$ hydrocarboxy group, a $C_1$ to $C_{12}$ hydrocarbylaminyl group, a $C_1$ to $C_{12}$ hydrocarbylsilyl group, a $C_1$ to $C_{12}$ hydrocarbylaminylsilyl group, $OBR^1_2$, or $OSO_2R^1$, wherein $R^1$ is a $C_1$ to $C_{12}$ hydrocarbyl group. In another aspect, each X independently can be H, $BH_4$, a halide, a $C_1$ to $C_{10}$ hydrocarbyl group, a $C_1$ to $C_{10}$ hydrocarboxy group, a $C_1$ to $C_{10}$ hydrocarbylaminyl group, a $C_1$ to $C_{10}$ hydrocarbylsilyl group, a $C_1$ to $C_{10}$ hydrocarbylaminylsilyl group, $OBR^1_2$, or $OSO_2R^1$, wherein $R^1$ is a $C_1$ to $C_{10}$ hydrocarbyl group. In yet another aspect, each X independently can be H, $BH_4$, a halide, a $C_1$ to $C_8$ hydrocarbyl group, a $C_1$ to $C_8$ hydrocarboxy group, a $C_1$ to $C_8$ hydrocarbylaminyl group, a $C_1$ to $C_8$ hydrocarbylsilyl group, a $C_1$ to $C_8$ hydrocarbylaminylsilyl group, $OBR^1_2$, or $OSO_2R^1$, wherein $R^1$ is a $C_1$ to $C_8$ hydrocarbyl group. In still another aspect, each X independently can be a halide or a $C_1$ to $C_{18}$ hydrocarbyl group. For example, each X can be Cl.

The hydrocarbyl group which can be an X (one or both) in formula (B) can be a $C_1$ to $C_{36}$ hydrocarbyl group, including, but not limited to, a $C_1$ to $C_{36}$ alkyl group, a $C_2$ to $C_{36}$ alkenyl group, a $C_4$ to $C_{36}$ cycloalkyl group, a $C_6$ to $C_{36}$ aryl group, or a $C_7$ to $C_{36}$ aralkyl group. For instance, each X independently can be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, each X independently can be a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; alternatively, each X independently can be a $C_1$ to $C_{10}$ alkyl group, a $C_2$ to $C_{10}$ alkenyl group, a $C_4$ to $C_{10}$ cycloalkyl group, a $C_6$ to $C_{10}$ aryl group, or a $C_7$ to $C_{10}$ aralkyl group; or alternatively, each X independently can be a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be an X in formula (B) can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be an X in formula (B) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

Suitable alkenyl groups which can be an X in formula (B) can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. In one aspect, each X in formula (B) independently can be an ethenyl group, a propenyl group, a butenyl group, a pentenyl group, a hexenyl group, a heptenyl group, an octenyl group, a nonenyl group, or a decenyl group, while in another aspect, each X in formula (B) independently can be an ethenyl group, a propenyl group, a butenyl group, a pentenyl group, or a hexenyl group. For example, an X can be an ethenyl group; alternatively, a propenyl group; alternatively, a butenyl group; alternatively, a pentenyl group; or alternatively, a hexenyl group. In yet another aspect, an X can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group. Illustrative terminal alkenyl groups can include, but are not limited to, a prop-2-en-1-yl group, a bute-3-en-1-yl group, a pent-4-en-1-yl group, a hex-5-en-1-yl group, a hept-6-en-1-yl group, an octe-7-en-1-yl group, a non-8-en-1-yl group, a dece-9-en-1-yl group, and so forth.

Each X in formula (B) independently can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, an X in formula (B) can be a cyclopentyl group, a substituted cyclopentyl group, a cyclohexyl group, or a substituted cyclohexyl group. Moreover, each X in formula (B) independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be an X in formula (B).

In some aspects, the aryl group which can be an X in formula (B) can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be an X in formula (B).

In an aspect, the substituted phenyl group which can be an X in formula (B) can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be an X in formula (B).

In some aspects, the aralkyl group which can be an X in formula (B) can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be an X in formula (B).

In an aspect, each non-hydrogen substituent(s) for the substituted cycloalkyl group, substituted aryl group, or substituted aralkyl group which can be an X in formula (B) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be an X in formula (B). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like. Furthermore, the hydrocarbyl substituent can be a benzyl group, a phenyl group, a tolyl group, or a xylyl group, and the like.

A hydrocarboxy group is used generically herein to include, for instance, alkoxy, aryloxy, aralkoxy, -(alkyl, aryl, or aralkyl)-O-(alkyl, aryl, or aralkyl) groups, and —O(CO)-(hydrogen or hydrocarbyl) groups, and these groups can comprise up to about 36 carbon atoms (e.g., $C_1$ to $C_{36}$, $C_1$ to $C_{18}$, $C_1$ to $C_{10}$, or $C_1$ to $C_8$ hydrocarboxy groups). Illustrative and non-limiting examples of hydrocarboxy groups which can be an X in formula (B) can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, and the like. In an aspect, the hydrocarboxy group which can be an X in formula (B) can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; or alternatively, a benzoate group.

The term hydrocarbylaminyl group is used generically herein to refer collectively to, for instance, alkylaminyl, arylaminyl, aralkylaminyl, dialkylaminyl, diarylaminyl, diaralkylaminyl, and -(alkyl, aryl, or aralkyl)-N-(alkyl, aryl, or aralkyl) groups, and unless otherwise specified, the hydrocarbylaminyl groups which can be an X in formula (B) can comprise up to about 36 carbon atoms (e.g., $C_1$ to $C_{36}$, $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group which can be an X in formula (B) can be, for instance, a methylaminyl group (—$NHCH_3$), an ethylaminyl group (—$NHCH_2CH_3$), an n-propylaminyl group (—$NHCH_2CH_2CH_3$), an iso-propylaminyl group (—$NHCH(CH_3)_2$), an n-butylaminyl group (—$NHCH_2CH_2CH_2CH_3$), a t-butylaminyl group (—$NHC(CH_3)_3$), an n-pentylaminyl group (—$NHCH_2CH_2CH_2CH_2CH_3$), a neo-pentylaminyl group (—$NHCH_2C(CH_3)_3$), a phenylaminyl group (—$NHC_6H_5$), a tolylaminyl group (—$NHC_6H_4CH_3$), or a xylylaminyl group (—$NHC_6H_3(CH_3)_2$); alternatively, a methylaminyl group; alternatively, an ethylaminyl group; alternatively, a propylaminyl group; or alternatively, a phenylaminyl group. In other aspects, the hydrocarbylaminyl group which can be an X in formula (B) can be, for instance, a dimethylaminyl group (—$N(CH_3)_2$), a diethylaminyl group (—$N(CH_2CH_3)_2$), a di-n-propylaminyl group (—$N(CH_2CH_2CH_3)_2$), a di-iso-propylaminyl group (—$N(CH(CH_3)_2)_2$), a di-n-butylaminyl group (—$N(CH_2CH_2CH_2CH_3)_2$), a di-t-butylaminyl group (—$N(C(CH_3)_3)_2$), a di-n-pentylaminyl group (—$N(CH_2CH_2CH_2CH_2CH_3)_2$), a di-neo-pentylaminyl group (—$N(CH_2C(CH_3)_3)_2$), a di-phenylaminyl group (—$N(C_6H_5)_2$), a di-tolylaminyl group (—$N(C_6H_4CH_3)_2$), or a di-xylylaminyl group (—$N(C_6H_3(CH_3)_2)_2$); alternatively, a dimethylaminyl group; alternatively, a di-ethylaminyl group; alternatively, a di-n-propylaminyl group; or alternatively, a di-phenylaminyl group.

In accordance with some aspects disclosed herein, each X independently can be a $C_1$ to $C_{36}$ hydrocarbylsilyl group; alternatively, a $C_1$ to $C_{24}$ hydrocarbylsilyl group; alternatively, a $C_1$ to $C_{18}$ hydrocarbylsilyl group; or alternatively, a $C_1$ to $C_8$ hydrocarbylsilyl group. In an aspect, each hydrocarbyl (one or more) of the hydrocarbylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). As used herein, hydrocarbylsilyl is intended to cover (mono) hydrocarbylsilyl (—$SiH_2R$), dihydrocarbylsilyl (—$SiHR_2$), and trihydrocarbylsilyl (—$SiR_3$) groups, with R being a hydrocarbyl group. In one aspect, the hydrocarbylsilyl group can be a $C_3$ to $C_{36}$ or a $C_3$ to $C_{18}$ trihydrocarbylsilyl group, such as, for example, a trialkylsilyl group or a triphenylsilyl group. Illustrative and non-limiting examples of hydrocarbylsilyl groups which can be an X in formula (B) can include, but are not limited to, trimethylsilyl, triethylsilyl, tripropylsilyl (e.g., triisopropylsilyl), tributylsilyl, tripentylsilyl, triphenylsilyl, allyldimethylsilyl, and the like.

A hydrocarbylaminylsilyl group is used herein to refer to groups containing at least one hydrocarbon moiety, at least one N atom, and at least one Si atom. Illustrative and non-limiting examples of hydrocarbylaminylsilyl groups which can be an X include, but are not limited to, —$N(SiMe_3)_2$, —$N(SiEt_3)_2$, and the like. Unless otherwise specified, the hydrocarbylaminylsilyl groups which can be an X can comprise up to about 36 carbon atoms (e.g., $C_1$ to $C_{36}$, $C_1$ to $C_{18}$, $C_1$ to $C_{12}$, or $C_1$ to $C_8$ hydrocarbylaminylsilyl groups). In an aspect, each hydrocarbyl (one or more) of the hydrocarbylaminylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). Moreover, hydrocarbylaminylsilyl is intended to cover —$NH(SiH_2R)$, —$NH(SiHR_2)$, —$NH(SiR_3)$, —$N(SiH_2R)_2$, —$N(SiHR_2)_2$, and —$N(SiR_3)_2$ groups, among others, with R being a hydrocarbyl group.

In an aspect, each X independently can be —$OBR^1_2$ or —$OSO_2R^1$, wherein $R^1$ is a $C_1$ to $C_{36}$ hydrocarbyl group, or alternatively, a $C_1$ to $C_{18}$ hydrocarbyl group. The hydrocarbyl group in $OBR^1_2$ and/or $OSO_2R^1$ independently can be any hydrocarbyl group disclosed herein, such as, for instance, a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; or alternatively, a $C_1$ to $C_8$ alkyl group, a $C_2$ to $C_8$ alkenyl group, a $C_5$ to $C_8$ cycloalkyl group, a $C_6$ to $C_8$ aryl group, or a $C_7$ to $C_8$ aralkyl group.

In one aspect, each X independently can be H, $BH_4$, a halide, or a $C_1$ to $C_{36}$ hydrocarbyl group, hydrocarboxy group, hydrocarbylaminyl group, hydrocarbylsilyl group, or hydrocarbylaminylsilyl group, while in another aspect, each X independently can be H, $BH_4$, or a $C_1$ to $C_{18}$ hydrocarboxy group, hydrocarbylaminyl group, hydrocarbylsilyl group, or hydrocarbylaminylsilyl group. In yet another aspect, each X independently can be a halide; alternatively, a $C_1$ to $C_{18}$ hydrocarbyl group; alternatively, a $C_1$ to $C_{18}$ hydrocarboxy group; alternatively, a $C_1$ to $C_{18}$ hydrocarbylaminyl group; alternatively, a $C_1$ to $C_{18}$ hydrocarbylsilyl group; or alternatively, a $C_1$ to $C_{18}$ hydrocarbylaminylsilyl group. In still another aspect, both X's can be H; alternatively, F; alternatively, Cl; alternatively, Br; alternatively, I; alternatively, $BH_4$; alternatively, a $C_1$ to $C_{18}$ hydrocarbyl group; alternatively, a $C_1$ to $C_{18}$ hydrocarboxy group; alternatively, a $C_1$ to $C_{18}$ hydrocarbylaminyl group; alternatively, a $C_1$ to $C_{18}$ hydrocarbylsilyl group; or alternatively, a $C_1$ to $C_{18}$ hydrocarbylaminylsilyl group.

Each X independently can be, in some aspects, H, a halide, methyl, phenyl, benzyl, an alkoxy, an aryloxy, acetylacetonate, formate, acetate, stearate, oleate, benzoate, an alkylaminyl, a dialkylaminyl, a trihydrocarbylsilyl, or a hydrocarbylaminylsilyl; alternatively, H, a halide, methyl, phenyl, or benzyl; alternatively, an alkoxy, an aryloxy, or acetylacetonate; alternatively, an alkylaminyl or a dialkylaminyl; alternatively, a trihydrocarbylsilyl or hydrocarbylaminylsilyl; alternatively, H or a halide; alternatively, methyl, phenyl, benzyl, an alkoxy, an aryloxy, acetylacetonate, an alkylaminyl, or a dialkylaminyl; alternatively, H; alternatively, a halide; alternatively, methyl; alternatively, phenyl; alternatively, benzyl; alternatively, an alkoxy; alternatively, an aryloxy; alternatively, acetylacetonate; alternatively, an alkylaminyl; alternatively, a dialkylaminyl; alternatively, a trihydrocarbylsilyl; or alternatively, a hydrocarbylaminylsilyl. In these and other aspects, the alkoxy, aryloxy, alkylaminyl, dialkylaminyl, trihydrocarbylsilyl, and hydrocarbylaminylsilyl can be a $C_1$ to $C_{36}$, a $C_1$ to $C_{18}$, a $C_1$ to $C_{12}$, or a $C_1$ to $C_8$ alkoxy, aryloxy, alkylaminyl, dialkylaminyl, trihydrocarbylsilyl, and hydrocarbylaminylsilyl.

Moreover, each X independently can be, in certain aspects, a halide or a $C_1$ to $C_{18}$ hydrocarbyl group; alternatively, a halide or a $C_1$ to $C_8$ hydrocarbyl group; alternatively, F, Cl, Br, I, methyl, benzyl, or phenyl; alternatively, Cl, methyl, benzyl, or phenyl; alternatively, a $C_1$ to $C_{18}$ alkoxy, aryloxy, alkylaminyl, dialkylaminyl, trihydrocarbylsilyl, or hydrocarbylaminylsilyl group; alternatively, a $C_1$ to $C_8$ alkoxy, aryloxy, alkylaminyl, dialkylaminyl, trihydrocarbylsilyl, or hydrocarbylaminylsilyl group; or alternatively, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

In formula (B), $Cp^1$ and $Cp^2$ independently can be a cyclopentadienyl, indenyl, or fluorenyl group (and the cyclopentadienyl, indenyl, or fluorenyl group can be substituted or unsubstituted, unless otherwise specified). In one aspect, for instance, $Cp^1$ can be a cyclopentadienyl group, and $Cp^2$ can be a cyclopentadienyl group. In another aspect, $Cp^1$ can be a cyclopentadienyl group, and $Cp^2$ can be an indenyl group. In yet another aspect, $Cp^1$ can be an indenyl group, and $Cp^2$ can be an indenyl group. In still another aspect, $Cp^1$ can be a cyclopentadienyl group, and $Cp^2$ can be a fluorenyl group. In these and other aspects, $Cp^1$ can be unsubstituted, or $Cp^2$ can be unsubstituted, or both $Cp^1$ and $Cp^2$ can be unsubstituted (in this terminology, the bridging group is not considered to be a substitution).

Consistent with other aspects of this invention, $Cp^1$ can be substituted with any suitable substituent, any suitable number of substituents, and at any suitable position(s) that conforms to the rules of chemical valence, and/or $Cp^2$ can be substituted with any suitable substituent, any suitable number of substituents, and at any suitable position(s) that conforms to the rules of chemical valence.

Accordingly, $Cp^1$ can contain a substituent (one or more) such as H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group. Similarly, $Cp^2$ can contain a substituent (one or more) such as H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group. Hence, each substituent independently can be H; alternatively, a halide; alternatively, a $C_1$ to $C_{18}$ hydrocarbyl group; alternatively, a $C_1$ to $C_{18}$ halogenated hydrocarbyl group; alternatively, a $C_1$ to $C_{18}$ hydrocarboxy group; alternatively, a $C_1$ to $C_{18}$ hydrocarbylsilyl group; alternatively, a $C_1$ to $C_{12}$ hydrocarbyl group or a $C_1$ to $C_{12}$ hydrocarbylsilyl group; or alternatively, a $C_1$ to $C_8$ alkyl group or a $C_3$ to $C_8$ alkenyl group. The halide, $C_1$ to $C_{36}$ hydrocarbyl group, $C_1$ to $C_{36}$ hydrocarboxy group, and $C_1$ to $C_{36}$ hydrocarbylsilyl group which can be a substituent on $Cp^1$ and/or $Cp^2$ in formula (B) can be any halide, $C_1$ to $C_{36}$ hydrocarbyl group, $C_1$ to $C_{36}$ hydrocarboxy group, and $C_1$ to $C_{36}$ hydrocarbylsilyl group described herein (e.g., as pertaining to X in formula (B)). A substituent on $Cp^1$ and/or $Cp^2$ independently can be, in certain aspects, a $C_1$ to $C_{36}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl ($CF_3$), and the like.

As a non-limiting example, each substituent on $Cp^1$ and/or $Cp^2$ independently can be H, Cl, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group (or other substituted aryl group), a benzyl group, a naphthyl group, a trimethylsilyl group, a triisopropylsilyl group, a triphenylsilyl group, an allyldimethylsilyl group, or a 1-methylcyclohexyl group; alternatively, H; alternatively, Cl; alternatively, $CF_3$; alternatively, a methyl group; alternatively, an ethyl group; alternatively, a propyl group; alternatively, a butyl group; alternatively, a pentyl group; alternatively, a hexyl group; alternatively, a heptyl group; alternatively, an octyl group, a nonyl group; alternatively, a decyl group; alternatively, an ethenyl group; alternatively, a propenyl group; alternatively, a butenyl group; alternatively, a pentenyl group; alternatively, a hexenyl group; alternatively, a heptenyl group; alternatively, an octenyl group; alternatively, a nonenyl group; alternatively, a decenyl group; alternatively, a phenyl group; alternatively, a tolyl group; alternatively, a benzyl group; alternatively, a naphthyl group; alternatively, a trimethylsilyl group; alternatively, a triisopropylsilyl group; alternatively, a triphenylsilyl group; alternatively, an allyldimethylsilyl group; or alternatively, a 1-methylcyclohexyl group.

In one aspect, for example, each substituent on $Cp^1$ and/or $Cp^2$ independently can be H or a $C_1$ to $C_{18}$ hydrocarbyl group; alternatively, a $C_1$ to $C_{10}$ hydrocarbyl group; alternatively, a $C_1$ to $C_8$ linear or branched alkyl group (e.g., a tert-butyl group); alternatively, a $C_3$ to $C_8$ terminal alkenyl group; alternatively, H, Cl, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, a naphthyl group, a trimethylsilyl group, a triisopropylsilyl group, a triphenylsilyl group, an allyldimethylsilyl group, or a 1-methylcyclohexyl group, and the like; alternatively, a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, or a benzyl group; alternatively, a methyl group, an ethyl group, a propyl group, a butyl group, a pentyl group, or a hexyl group; alternatively, a methyl group; alternatively, an ethyl group; alternatively, a propyl group; alternatively, a butyl group; or alternatively, a tert-butyl group.

In formula (B), $Cp^1$ can be a cyclopentadienyl or indenyl group optionally substituted with any substituent (i.e., one or more) disclosed herein, while $Cp^2$ can be a cyclopentadienyl or indenyl group with an alkenyl substituent. Further, $Cp^1$ can be a cyclopentadienyl group optionally substituted with any suitable substituent other than an alkenyl substituent, while $Cp^2$ can be an indenyl group with an alkenyl substituent. In these and other aspects, the alkenyl substituent can be at any suitable position on $Cp^2$ that conforms to the rules of chemical valence. In some aspects, $Cp^2$ has only one substituent, and that one substituent is an alkenyl substituent.

While not limited thereto, the alkenyl substituent can be a $C_2$ to $C_{18}$ alkenyl group, i.e., any $C_2$ to $C_{18}$ alkenyl group disclosed herein. For instance, the alkenyl substituent can be an ethenyl group, a propenyl group, a butenyl group, a pentenyl group, a hexenyl group, a heptenyl group, an octenyl group, a nonenyl group, or a decenyl group. In other aspects, the alkenyl substituent can be a $C_2$ to $C_{12}$ linear or branched alkenyl group; alternatively, a $C_2$ to $C_8$ linear or branched alkenyl group; alternatively, a $C_3$ to $C_{12}$ linear alkenyl group; alternatively, a $C_2$ to $C_8$ linear alkenyl group; alternatively, a $C_2$ to $C_8$ terminal alkenyl group; alternatively, a $C_3$ to $C_8$ terminal alkenyl group; or alternatively, a $C_3$ to $C_6$ terminal alkenyl group.

In accordance with non-limiting aspects of this invention, $Cp^2$ can be an indenyl group with only an alkenyl substituent, and $Cp^1$ can be an cyclopentadienyl or indenyl group that does not contain any substituents; or $Cp^2$ can be an indenyl group with an alkenyl substituent and one or more other substituents, and $Cp^1$ can be a cyclopentadienyl or indenyl group that does not contain an alkenyl substituent, but contains one or more other substituents; or $Cp^2$ can be an indenyl group with an alkenyl substituent and one or more other substituents, and $Cp^1$ can be a cyclopentadienyl or indenyl group that does not contain any substituents; or $Cp^2$ can be an indenyl group with an alkenyl substituent and one or more other substituents, and $Cp^1$ can be a cyclopentadienyl or indenyl group that contains one or more substituents.

In other aspects, $Cp^1$ can be a cyclopentadienyl or indenyl group optionally substituted with any substituent (i.e., one or more) disclosed herein, while $Cp^2$ can be a fluorenyl group optionally substituted with any substituent (i.e., one or more) disclosed herein. Further, $Cp^1$ can be a cyclopentadienyl group, optionally substituted, while $Cp^2$ can be an unsubstituted fluorenyl group or a fluorenyl group with one or more hydrocarbyl substituents, such as a $C_1$ to $C_8$ alkyl group. In these and other aspects, the hydrocarbyl substituent(s) can be at any suitable position on $Cp^2$ that conforms to the rules of chemical valence. In some aspects, $Cp^2$ has only two substituents, and both substituents are alkyl substituents.

In formula (B), E can be a bicyclic bridging group connected to $Cp^1$ and $Cp^2$, often a $C_7$ to $C_{18}$ bicyclic bridging group, a $C_7$ to $C_{12}$ bicyclic bridging group, or a $C_7$ to $C_{10}$ bicyclic bridging group. Consistent with aspects of the present invention, a single atom bridge connects $Cp^1$ and $Cp^2$, and the bridging atom is part of the bicyclic bridging group. Further, the bridging atom can be a carbon atom, and optionally, the bicyclic bridging group can contain one or more heteroatoms, although this is not a requirement.

In one aspect of this invention, for instance, E can be a saturated hydrocarbon group, while in another aspect, E can be an unsaturated hydrocarbon group, and in yet another aspect, E can be an aromatic hydrocarbon group. Moreover, in various aspects of this invention, the bridging group E in formula (B) can be a tetralin group; alternatively, a decalin group; alternatively, an indane group; alternatively, an indene group; alternatively, a norbornane group; alternatively, a norbornene group; alternatively, a norbornadiene group; or alternatively, a dicyclopentadiene group. Other suitable bicyclic bridging groups are readily apparent from this disclosure.

Illustrative and non-limiting examples of bicyclic bridged metallocene compounds can include the following compounds (tBu=tert-butyl; Et=ethyl; R=a hydrocarbyl substituent, such as a $C_1$ to $C_8$ alkyl group or a $C_3$ to $C_8$ alkenyl group; X is a monoanionic ligand, such as a halide, a $C_1$ to $C_8$ hydrocarbyl group, or a $C_1$ to $C_8$ hydrocarbylaminyl group):

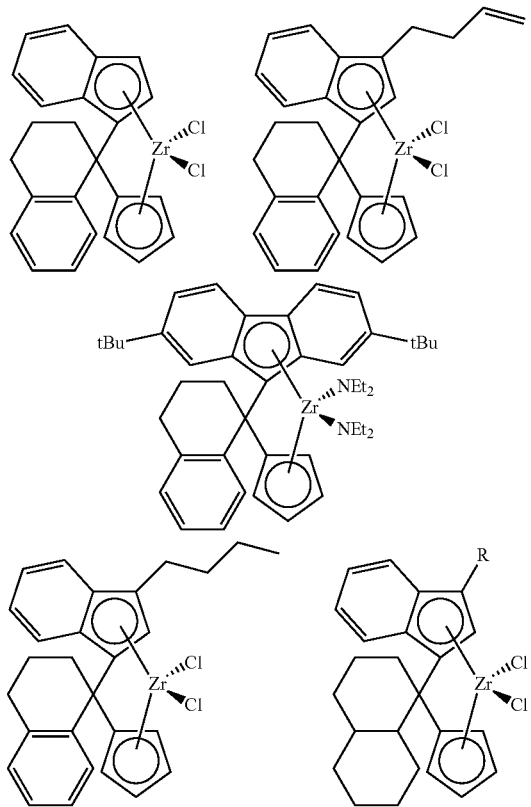

and the like.

Methods of making bicyclic bridged metallocene complexes of the present invention also are encompassed herein. These metallocene complexes can be synthesized by various suitable procedures, such as those described in U.S. Pat. Nos. 7,468,452 and 8,309,747, the disclosures of which are incorporated herein by reference in their entirety, and the procedures provided herein.

A representative and generalized synthesis scheme is provided below, where the bicyclic bridged metallocene compound can be synthesized in a multistep process. In a first step, an anion of $Cp^1$ (e.g., $Li^+(Cp^1)^-$, or $Cp^1$ in the presence of a strong base) can be contacted with

in a first solvent to form the following ligand compound,

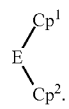 (A)

Next, an anion of the ligand compound of formula (A) can be contacted with $MX_4$ (each X independently can be any monoanionic ligand disclosed herein) in a second solvent (which can be the same as or different from the first solvent) to form the bicyclic bridged metallocene compound of formula (B):

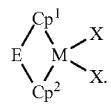 (B)

The stereoselective synthesis of metallocene complexes can be important, since polymerization behavior often is related to the metallocene structure. For the bicyclic bridged metallocene complexes disclosed herein, in which the bicyclic-bridged metallocene contains at least one asymmetric Cp unit (e.g., $Cp^1$ is a cyclopentadienyl ligand and $Cp^2$ is an indenyl ligand), two possible diastereomeric configurations of the bicyclic-bridged metallocene complex can exist depending on the orientation of the asymmetric Cp-type ligand relative to the extended ring system of the bicyclic bridging group. For some of the illustrative synthesis examples that follow, and unexpectedly, it can be seen that under certain conditions, isolation of both possible configurational diastereomers is possible: $M1\text{-}Cl_2$ in examples 1 and 3, and $M6\text{-}Cl_2$ in example 27, which both form nearly 1:1 mixtures of the two possible configurational diastereomers. In this disclosure, and also unexpectedly, it was found that the bicyclic bridged metallocene complexes can be formed selectively as a single diastereomer through the use of an ether solvent (e.g., a dialkyl ether) during conversion of the zirconium bis-amide structures to their respective zirconium dichlorides. This is demonstrated in examples 2 and 28 for metallocene compounds $M1\text{-}Cl_2$ and $M6\text{-}Cl_2$, respectively. In these examples, switching the solvent for the chlorination step from a hydrocarbon such as benzene or toluene, to an ether solvent such as diethyl ether, resulted in the selective synthesis of a single diastereomer for each of these bicyclic bridged metallocene complexes.

Also encompassed herein are ligand compounds which can be used to form metallocene compounds having formula (B). Such ligand compounds can have the following formula:

 (A)

The selections for $Cp^1$, $Cp^2$, and E in formula (A) are the same as those described herein for formula (B). Hence, in formula (A), $Cp^1$ and $Cp^2$ independently can be a cyclopentadienyl group, an indenyl group, or a fluorenyl group. Further, $Cp^1$ and $Cp^2$ can be unsubstituted or can be substituted with any suitable substituent, any suitable number of substituents, and at any suitable position(s) that conforms to the rules of chemical valence. The bicyclic bridging group E in formula (A) can be any suitable saturated, unsaturated, or aromatic $C_7$ to $C_{18}$, or $C_7$ to $C_{10}$, bicyclic bridging group.

Illustrative and non-limiting examples of bicyclic bridged ligand compounds can include the following compounds (tBu=tert-butyl):

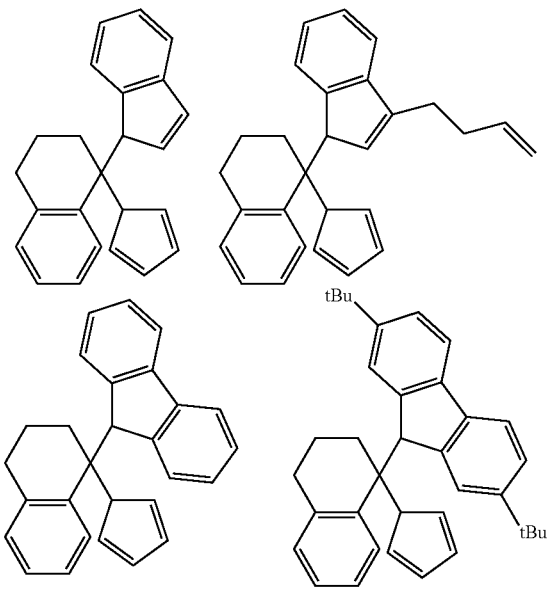

-continued

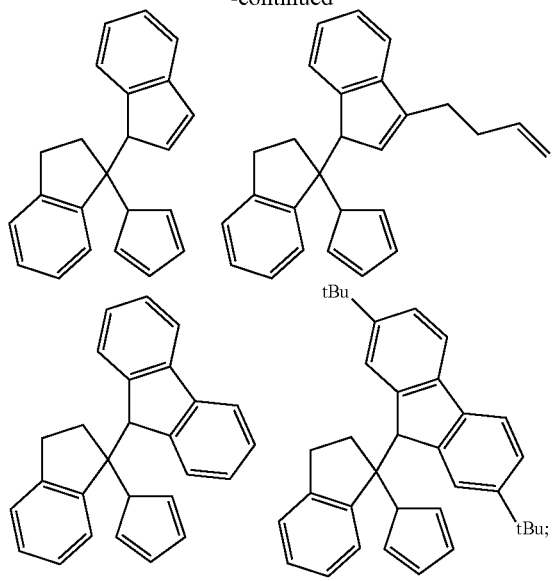

and the like.

Using analogous synthesis schemes to those provided herein, ligand and metallocene complexes with various bicyclic bridging groups can be derived, and complexes with indenyl, cyclopentadienyl, or fluorenyl groups with various substituents (such as alkyl and alkenyl substituents) can be derived. Moreover, using analogous synthesis schemes to those provided herein, metallocene complexes with monoanionic ligands other than Cl and hydrocarbylaminyl (e.g., hydrocarbyl, hydrocarbylsilyl, etc.) can be derived, and complexes with various transition metals can be derived.

Activator-Supports The present invention encompasses various catalyst compositions containing an activator-support. In one aspect, the activator-support can comprise a solid oxide treated with an electron-withdrawing anion. Alternatively, in another aspect, the activator-support can comprise a solid oxide treated with an electron-withdrawing anion, the solid oxide containing a Lewis-acidic metal ion. Non-limiting examples of suitable activator-supports are disclosed in, for instance, U.S. Pat. Nos. 7,294,599, 7,601,665, 7,884,163, 8,309,485, 8,623,973, 8,703,886, and 9,023,959, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form an activator-support, either singly or in combination, can include, but are not limited to, silica-alumina, silica-titania, silica-zirconia, alumina-titania, alumina-zirconia, zinc-aluminate, alumina-boria, silica-boria, aluminophosphate-silica, titania-zirconia, and the like. The solid oxide used herein also can encompass oxide materials such as silica-coated alumina, as described in U.S. Pat. No. 7,884,163 (e.g., Sasol Siral® 28, Sasol Siral® 40, etc.).

Accordingly, in one aspect, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another aspect, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another aspect, the solid oxide can comprise silica, alumina, titania, zirconia, magnesia, boria, zinc oxide, any mixed oxide thereof, or any combination thereof. In yet another aspect, the solid oxide can comprise silica-alumina, silica-coated alumina, silica-titania, silica-zirconia, alumina-boria, or any combination thereof. In still another aspect, the solid oxide can comprise alumina, silica-alumina, silica-coated alumina, or any mixture thereof; alternatively, alumina; alternatively, silica-alumina; or alternatively, silica-coated alumina.

The silica-alumina or silica-coated alumina solid oxide materials which can be used can have an silica content from about 5 to about 95% by weight. In one aspect, the silica content of these solid oxides can be from about 10 to about 80%, or from about 20% to about 70%, silica by weight. In another aspect, such materials can have silica contents ranging from about 15% to about 60%, from about 20% to about 50%, or from about 25% to about 45%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, and the like, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The activator-support generally can contain from about 1 to about 25 wt. % of the electron-withdrawing anion, based on the weight of the activator-support. In particular aspects provided herein, the activator-support can contain from about 1 to about 20 wt. %, from about 2 to about 20 wt. %, from about 3 to about 20 wt. %, from about 2 to about 15 wt. %, from about 3 to about 15 wt. %, from about 3 to about 12 wt. %, or from about 4 to about 10 wt. %, of the electron-withdrawing anion, based on the total weight of the activator-support.

In an aspect, the activator-support can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, and the like, as well as any mixture or combination thereof. In another aspect, the activator-support employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided-chlorided silica-coated alumina, fluorided silica-coated alumina, sulfated silica-coated alumina, and the like, as well as combinations thereof. In yet another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina.

Various processes can be used to form activator-supports useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, and the like, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing activator-supports (e.g., fluorided solid oxides, sulfated solid oxides, etc.) are well known to those of skill in the art.

Co-Catalysts

In certain aspects directed to catalyst compositions containing a co-catalyst, the co-catalyst can comprise a metal hydrocarbyl compound, examples of which include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some aspects, the metal of the metal hydrocarbyl can be a group 1, 2, 11, 12, 13, or 14 metal; alternatively, a group 13 or 14 metal; or alternatively, a group 13 metal. Hence, in some aspects, the metal of the metal hydrocarbyl (or non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some aspects, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In particular aspects directed to catalyst compositions containing a co-catalyst (e.g., the activator can comprise a solid oxide treated with an electron-withdrawing anion), the co-catalyst can comprise an aluminoxane compound (e.g., a supported aluminoxane), an organoboron or organoborate compound, an ionizing ionic compound, an organoaluminum compound, an organozinc compound, an organomagnesium compound, or an organolithium compound, and this includes any combinations of these materials. In one aspect, the co-catalyst can comprise an organoaluminum compound. In another aspect, the co-catalyst can comprise an aluminoxane compound, an organoboron or organoborate compound, an ionizing ionic compound, an organozinc compound, an organomagnesium compound, an organolithium compound, or any combination thereof. In yet another aspect, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof. Representative and non-limiting examples of aluminoxanes include methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Representative and non-limiting examples of organoboron/organoborate compounds include N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, tris(pentafluorophenyl)boron, tris[3,5-bis(trifluoromethyl)phenyl]boron, and the like, or mixtures thereof.

Examples of ionizing ionic compounds can include, but are not limited to, the following compounds: tri(n-butyl)ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis (trifluoromethyl)phenyl]borate, tropylium tetrakis(pentafluorophenyl) borate, lithium tetrakis(pentafluorophenyl) borate, lithium tetraphenylborate, lithium tetrakis(p-tolyl) borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis (pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis (pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis (3,5-dimethylphenyl)aluminate, potassium tetrafluoroaluminate, and the like, or combinations thereof.

Exemplary organozinc compounds which can be used as co-catalysts can include, but are not limited to, dimethylzinc, diethylzinc, dipropylzinc, dibutylzinc, dineopentylzinc, di(trimethylsilyl)zinc, di(triethyl silyl)zinc, di(triisoproplysilyl)zinc, di(triphenylsilyl)zinc, di(allyldimethylsilyl)zinc, di(trimethylsilylmethyl)zinc, and the like, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethyl silylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, and the like, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xyllithium, benzyllithium, (dimethylphenyl) methyllithium, allyllithium, and the like, or combinations thereof.

Co-catalysts that can be used in the catalyst compositions of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485, which are incorporated herein by reference in their entirety.

Olefin Monomers

Unsaturated reactants that can be employed with catalyst compositions and polymerization processes of this invention typically can include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally can contain a major amount of ethylene (>50 mole percent) and a minor amount of comonomer (<50 mole percent), though this is not a requirement. Comonomers that can be copolymerized with ethylene often can have from 3 to 20 carbon atoms, or from 3 to 10 carbon atoms, in their molecular chain.

Acyclic, cyclic, polycyclic, terminal (a), internal, linear, branched, substituted, unsubstituted, functionalized, and non-functionalized olefins can be employed in this invention. For example, typical unsaturated compounds that can be polymerized with the catalyst compositions of this invention can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described herein. Styrene can also be employed as a monomer in the present invention. In an aspect, the olefin monomer can comprise a $C_2$-$C_{20}$ olefin; alternatively, a $C_2$-$C_{20}$ alpha-olefin; alternatively, a $C_2$-$C_{10}$ olefin; alternatively, a $C_2$-$C_{10}$ alpha-olefin; alternatively, the olefin monomer can comprise ethylene; or alternatively, the olefin monomer can comprise propylene.

When a copolymer (or alternatively, a terpolymer) is desired, the olefin monomer and the olefin comonomer independently can comprise, for example, a $C_2$-$C_{20}$ alpha-olefin. In some aspects, the olefin monomer can comprise ethylene or propylene, which is copolymerized with at least one comonomer (e.g., a $C_2$-$C_{20}$ alpha-olefin, a $C_3$-$C_{20}$ alpha-olefin, etc.). According to one aspect of this invention, the olefin monomer used in the polymerization process can comprise ethylene. In this aspect, examples of suitable olefin comonomers can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to another aspect of the present invention, the olefin monomer can comprise ethylene, and the comonomer can comprise a $C_3$-$C_{10}$ alpha-olefin; alternatively, the comonomer can comprise 1-butene, 1-pentene, 1-hexene, 1-octene, 1-decene, styrene, or any combination thereof; alternatively, the comonomer can comprise 1-butene, 1-hexene, 1-octene, or any combination thereof; alternatively, the comonomer can comprise 1-butene; alternatively, the comonomer can comprise 1-hexene; or alternatively, the comonomer can comprise 1-octene.

Generally, the amount of comonomer introduced into a polymerization reactor system to produce a copolymer can be from about 0.01 to about 50 weight percent of the comonomer based on the total weight of the monomer and comonomer. According to another aspect of the present invention, the amount of comonomer introduced into a polymerization reactor system can be from about 0.01 to about 40 weight percent comonomer based on the total weight of the monomer and comonomer. In still another aspect, the amount of comonomer introduced into a polymerization reactor system can be from about 0.1 to about 35 weight percent comonomer based on the total weight of the monomer and comonomer. Yet, in another aspect, the amount of comonomer introduced into a polymerization reactor system can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might.

According to one aspect of the present invention, at least one monomer/reactant can be ethylene (or propylene), so the polymerization reaction can be a homopolymerization involving only ethylene (or propylene), or a copolymerization with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Catalyst Compositions

In some aspects, the present invention employs catalyst compositions containing a bicyclic bridged metallocene compound and an activator (one or more than one). These catalyst compositions can be utilized to produce polyolefins—homopolymers, copolymers, and the like—for a variety of end-use applications. Bicyclic bridged metallocene compounds are discussed hereinabove. In aspects of the present invention, it is contemplated that the catalyst composition can contain more than one bicyclic bridged metallocene compound. Further, additional catalytic compounds—other than those specified as a bicyclic bridged metallocene compound—can be employed in the catalyst compositions and/or the polymerization processes, provided that the additional catalytic compound does not detract from the advantages disclosed herein. Additionally, more than one activator also can be utilized.

Generally, catalyst compositions of the present invention comprise a bicyclic bridged metallocene compound having formula (B) and an activator. In aspects of the invention, the activator can comprise an activator-support (e.g., an activator-support comprising a solid oxide treated with an electron-withdrawing anion). Activator-supports useful in the present invention are disclosed herein. Optionally, such catalyst compositions can further comprise one or more than one co-catalyst compound or compounds (suitable co-catalysts, such as organoaluminum compounds, also are discussed herein). Thus, a catalyst composition of this invention can comprise a bicyclic bridged metallocene compound, an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, and the like, or combinations thereof; or alternatively, a fluorided solid oxide and/or a sulfated solid oxide. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Accordingly, a catalyst composition consistent with aspects of the invention can comprise (or consist essentially of, or consist of) a bicyclic bridged metallocene compound; sulfated alumina (or fluorided-chlorided silica-coated alumina, or fluorided silica-coated alumina); and triethylaluminum (or triisobutylaluminum).

In another aspect of the present invention, a catalyst composition is provided which comprises a bicyclic bridged metallocene compound, an activator-support, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, discussed below, in the absence of these additional materials. For example, a catalyst composition of the present invention can consist essentially of a bicyclic bridged metallocene compound, an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising a bicyclic bridged metallocene compound and an activator-support can further comprise an optional co-catalyst. Suitable co-catalysts in this aspect can include, but are not limited to, aluminoxane compounds, organoboron or organoborate compounds, ionizing ionic compounds, organoaluminum compounds, organozinc compounds, organomagnesium compounds, organolithium compounds, and the like, or any combination thereof; or alternatively, organoaluminum compounds, organozinc compounds, organomagnesium compounds, organolithium compounds, or any combination thereof. More than one co-catalyst can be present in the catalyst composition.

In a different aspect, a catalyst composition is provided which does not require an activator-support. Such a catalyst composition can comprise a bicyclic bridged metallocene compound and an activator, wherein the activator can comprise an aluminoxane compound (e.g., a supported aluminoxane), an organoboron or organoborate compound, an ionizing ionic compound, or combinations thereof; alternatively, an aluminoxane compound; alternatively, an organoboron or organoborate compound; or alternatively, an ionizing ionic compound.

In a particular aspect contemplated herein, the catalyst composition is a catalyst composition comprising an activator (one or more than one) and only one bicyclic bridged metallocene compound having formula (B). In these and other aspects, the catalyst composition can comprise an activator (e.g., an activator-support comprising a solid oxide treated with an electron-withdrawing anion), only one bicyclic bridged metallocene compound, and a co-catalyst (one or more than one), such as an organoaluminum compound.

This invention further encompasses methods of making these catalyst compositions, such as, for example, contacting the respective catalyst components in any order or sequence. In one aspect, the catalyst composition can be produced by a process comprising contacting the metallocene compound and the activator, while in another aspect, the catalyst composition can be produced by a process comprising contacting, in any order, the metallocene compound, the activator, and the co-catalyst.

Generally, the weight ratio of organoaluminum compound to activator-support can be in a range from about 10:1 to about 1:1000. If more than one organoaluminum compound and/or more than one activator-support are employed, this ratio is based on the total weight of each respective component. In another aspect, the weight ratio of the organoaluminum compound to the activator-support can be in a range from about 3:1 to about 1:500, or from about 1:10 to about 1:350.

In some aspects of this invention, the weight ratio of metallocene compound to activator-support can be in a range from about 1:1 to about 1:1,000,000. If more than one metallocene compound and/or more than activator-support is/are employed, this ratio is based on the total weights of the respective components. In another aspect, this weight ratio can be in a range from about 1:5 to about 1:100,000, or from about 1:10 to about 1:10,000. Yet, in another aspect, the weight ratio of the metallocene compound to the activator-support can be in a range from about 1:20 to about 1:1000.

Catalyst compositions of the present invention generally have a catalyst activity greater than about 50,000 grams, greater than about 75,000 grams, greater than about 100,000 grams, greater than about 125,000 grams, etc., of ethylene polymer (homopolymer or copolymer, as the context requires) per gram of the bicyclic bridged metallocene compound per hour (abbreviated g/g/h). In another aspect, the catalyst activity can be greater than about 150,000, greater than about 175,000, or greater than about 200,000 g/g/h, and often can range up to 500,000-2,000,000 g/g/h. These activities are measured under slurry polymerization conditions, with a triisobutylaluminum co-catalyst, using isobutane as the diluent, at a polymerization temperature of 80° C. and a reactor pressure of 340 psig. Additionally, in some aspects, the activator can comprise an activator-support, such as sulfated alumina, fluorided-chlorided silica-coated alumina, or fluorided silica-coated alumina, although not limited thereto.

Polymerization Processes

Catalyst compositions of the present invention can be used to polymerize olefins to form homopolymers, copolymers, terpolymers, and the like. One such process for polymerizing olefins in the presence of a catalyst composition of the present invention can comprise contacting the catalyst composition with an olefin monomer and optionally an olefin comonomer (one or more) in a polymerization reactor system under polymerization conditions to produce an olefin polymer, wherein the catalyst composition can comprise a bicyclic bridged metallocene compound, an activator, and an optional co-catalyst. Suitable bicyclic bridged metallocene compounds, activators, and co-catalysts are discussed herein.

In accordance with one aspect of the invention, the polymerization process can employ a catalyst composition comprising a bicyclic bridged metallocene compound having formula (B) and an activator, wherein the activator comprises an activator-support. The catalyst composition, optionally, can further comprise one or more than one organoaluminum compound or compounds (or other suitable co-catalyst). Thus, a process for polymerizing olefins in the presence of a catalyst composition can employ a catalyst composition comprising a bicyclic bridged metallocene compound, an activator-support, and an organoaluminum compound. In some aspects, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, and the like, or combinations thereof; or alternatively, a fluorided solid oxide and/or a sulfated solid oxide. In some aspects, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof.

In accordance with another aspect of the invention, the polymerization process can employ a catalyst composition comprising a bicyclic bridged metallocene, an activator-support, and an optional co-catalyst, wherein the co-catalyst can comprise an aluminoxane compound, an organoboron or organoborate compound, an ionizing ionic compound, an organoaluminum compound, an organozinc compound, an organomagnesium compound, or an organolithium compound, or any combination thereof. Hence, aspects of this invention are directed to a process for polymerizing olefins in the presence of a catalyst composition, the process comprising contacting a catalyst composition with an olefin monomer and optionally an olefin comonomer (one or more) under polymerization conditions to produce an olefin polymer, and the catalyst composition can comprise a bicyclic bridged metallocene compound, an activator-support, and an aluminoxane compound; alternatively, a bicyclic bridged metallocene compound, an activator-support, and an organoboron or organoborate compound; alternatively, a bicyclic bridged metallocene compound, an activator-support, and an ionizing ionic compound; alternatively, a bicyclic bridged metallocene compound, an activator-support, and an organoaluminum compound; alternatively, a bicyclic bridged metallocene compound, an activator-support, and an organozinc compound; alternatively, a bicyclic bridged metallocene compound, an activator-support, and an organomagnesium compound; or alternatively, a bicyclic bridged metallocene compound, an activator-support, and an organolithium compound. Furthermore, more than one co-catalyst can be employed, e.g., an organoaluminum compound and an aluminoxane compound, an organoaluminum compound and an ionizing ionic compound, etc.

In accordance with another aspect of the invention, the polymerization process can employ a catalyst composition comprising only one bicyclic bridged metallocene compound, an activator-support, and an organoaluminum compound.

In accordance with yet another aspect of the invention, the polymerization process can employ a catalyst composition comprising a bicyclic bridged metallocene compound and an activator, wherein the activator comprises an aluminoxane compound, an organoboron or organoborate compound, an ionizing ionic compound, or combinations thereof; alternatively, an aluminoxane compound; alternatively, an organoboron or organoborate compound; or alternatively, an ionizing ionic compound.

The catalyst compositions of the present invention are intended for any olefin polymerization method using various types of polymerization reactor systems and reactors. The polymerization reactor system can include any polymerization reactor capable of polymerizing olefin monomers and comonomers (one or more than one comonomer) to produce homopolymers, copolymers, terpolymers, and the like. The various types of reactors include those that can be referred to as a loop reactor, slurry reactor, gas-phase reactor, solution reactor, high pressure reactor, tubular reactor, autoclave reactor, and the like, or combinations thereof. Suitable polymerization conditions are used for the various reactor types. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes can use intermittent or continuous product discharge. Processes can also include partial or full direct recycle of unreacted monomer, unreacted comonomer, and/or diluent.

Polymerization reactor systems of the present invention can comprise one type of reactor in a system or multiple reactors of the same or different type (e.g., a single reactor, dual reactor, more than two reactors). Production of polymers in multiple reactors can include several stages in at least two separate polymerization reactors interconnected by a transfer device making it possible to transfer the polymers resulting from the first polymerization reactor into the second reactor. The desired polymerization conditions in one of the reactors can be different from the operating conditions of the other reactor(s). Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors, or a combination of high pressure with loop and/or gas phase reactors. The multiple reactors can be operated in series, in parallel, or both. Accordingly, the present invention encompasses polymerization reactor systems comprising a single reactor, comprising two reactors, and comprising more than two reactors. The polymerization reactor system can comprise a slurry reactor, a gas-phase reactor, a solution reactor, in certain aspects of this invention, as well as multi-reactor combinations thereof.

According to one aspect of the invention, the polymerization reactor system can comprise at least one loop slurry reactor comprising vertical or horizontal loops. Monomer, diluent, catalyst, and comonomer can be continuously fed to a loop reactor where polymerization occurs. Generally, continuous processes can comprise the continuous introduction of monomer/comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including, but not limited to, flashing that can include any combination of heat addition and pressure reduction, separation by cyclonic action in either a cyclone or hydrocyclone, or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, 6,833,415, and 8,822,608, each of which is incorporated herein by reference in its entirety.

Suitable diluents used in slurry polymerization include, but are not limited to, the monomer being polymerized and hydrocarbons that are liquids under polymerization conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used, such as can be employed in the bulk polymerization of propylene to form polypropylene homopolymers.

According to yet another aspect of this invention, the polymerization reactor system can comprise at least one gas phase reactor. Such systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, 5,436,304, 7,531,606, and 7,598,327, each of which is incorporated by reference in its entirety herein.

According to still another aspect of the invention, a high pressure polymerization reactor can comprise a tubular reactor or an autoclave reactor. Tubular reactors can have several zones where fresh monomer, initiators, or catalysts are added. Monomer can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately to obtain optimal polymerization reaction conditions.

According to yet another aspect of the invention, the polymerization reactor system can comprise a solution polymerization reactor wherein the monomer (and comonomer, if used) are contacted with the catalyst composition by suitable stirring or other means. A carrier comprising an inert organic diluent or excess monomer can be employed. If desired, the monomer/comonomer can be brought in the vapor phase into contact with the catalytic reaction product, in the presence or absence of liquid material. The polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactor systems suitable for the present invention can further comprise any combination of at least one raw material feed system, at least one feed system for catalyst or catalyst components, and/or at least one polymer recovery system. Suitable reactor systems for the present invention can further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature can be any temperature below the de-polymerization temperature according to the Gibbs Free energy equation. Typically, this includes from about 35° C. to about 280° C., for example, or from about 50° C. to about 175° C., depending upon the type of polymerization reactor(s). In some reactor systems, the polymerization temperature generally can fall within a range from about 60° C. to about 120° C., or from about 70° C. to about 100° C. Various polymerization conditions can be held substantially constant, for example, for the production of a particular grade of olefin polymer.

Suitable pressures will also vary according to the reactor and polymerization type. The pressure for liquid phase polymerizations in a loop reactor is typically less than 1000 psig (6.9 MPa). The pressure for gas phase polymerization is usually at about 200 to 500 psig (1.4 MPa to 3.4 MPa). High pressure polymerization in tubular or autoclave reactors is generally conducted at about 20,000 to 75,000 psig (138 to 517 MPa). Polymerization reactors can also be operated in a supercritical region occurring at generally higher temperatures and pressures (for instance, above 92° C. and 700 psig (4.83 MPa)). Operation above the critical point of a pressure/temperature diagram (supercritical phase) can offer advantages to the polymerization reaction process.

Aspects of this invention are directed to olefin polymerization processes comprising contacting a catalyst composition with an olefin monomer and, optionally, an olefin comonomer under polymerization conditions to produce an olefin polymer. The olefin polymer (e.g., ethylene homopolymer, ethylene copolymer, etc.) produced by the process can have any of the polymer properties disclosed herein, for example, a melt index in a range from about 250 to about 2000 g/10 min (or from about 400 to about 1000 g/10 min, or greater than 500 g/10 min), and/or a density in a range from about 0.87 to about 0.96 g/cm$^3$ (or from about 0.89 to about 0.93 g/cm$^3$), and/or a Mw in a range from about 10,000 to about 25,000 g/mol (or from about 12,000 to about 23,000 g/mol), and/or an Mn in a range from about 3,000 to about 13,000 g/mol (or from about 4,500 to about 10,000 g/mol), and/or a ratio of Mw/Mn in a range from about 2 to about 3.5 (or from about 2 to about 2.5). Such polymer properties can be produced, for instance, using a catalyst system containing an aromatic bicyclic bridged metallocene.

Another olefin polymer (e.g., ethylene homopolymer, ethylene copolymer, etc.) produced by the process can have any of the polymer properties disclosed herein, for example, a melt index in a range from about 10 to about 200 g/10 min (or from about 20 to about 150 g/10 min), and/or a density in a range from about 0.87 to about 0.96 g/cm$^3$ (or from about 0.89 to about 0.93 g/cm$^3$), and/or a Mw in a range from about 27,000 to about 65,000 g/mol (or from about 30,000 to about 60,000 g/mol), and/or an Mn in a range from about 12,000 to about 35,000 g/mol (or from about 14,000 to about 30,000 g/mol), and/or a ratio of Mw/Mn in a range from about 2 to about 3.5 (or from about 2 to about 2.5). Such polymer properties can be produced, for instance, using a catalyst system containing a saturated bicyclic bridged metallocene.

Aspects of this invention also are directed to olefin polymerization processes conducted in the absence of added hydrogen. An olefin polymerization process of this invention can comprise contacting a catalyst composition with an olefin monomer and optionally an olefin comonomer in a polymerization reactor system under polymerization conditions to produce an olefin polymer, wherein the catalyst composition can comprise a bicyclic bridged metallocene, an activator, and an optional co-catalyst, and wherein the polymerization process is conducted in the absence of added hydrogen (no hydrogen is added to the polymerization reactor system). As one of ordinary skill in the art would recognize, hydrogen can be generated in-situ by metallocene catalyst compositions in various olefin polymerization processes, and the amount generated can vary depending upon the specific catalyst composition and metallocene compound employed, the type of polymerization process used, the polymerization reaction conditions utilized, and so forth.

In other aspects, it may be desirable to conduct the polymerization process in the presence of a certain amount of added hydrogen. Accordingly, an olefin polymerization process of this invention can comprise contacting a catalyst composition with an olefin monomer and optionally an olefin comonomer in a polymerization reactor system under polymerization conditions to produce an olefin polymer, wherein the catalyst composition comprises a bicyclic bridged metallocene, an activator, and an optional co-catalyst, and wherein the polymerization process is conducted in the presence of added hydrogen (hydrogen is added to the polymerization reactor system). For example, the ratio of hydrogen to the olefin monomer in the polymerization process can be controlled, often by the feed ratio of hydrogen to the olefin monomer entering the reactor. The added hydrogen to olefin monomer ratio in the process can be controlled at a weight ratio which falls within a range from about 25 ppm to about 1500 ppm, from about 50 to about 1000 ppm, or from about 100 ppm to about 750 ppm.

In some aspects of this invention, the feed or reactant ratio of hydrogen to olefin monomer can be maintained substantially constant during the polymerization run for a particular polymer grade. That is, the hydrogen:olefin monomer ratio can be selected at a particular ratio within a range from about 5 ppm up to about 1000 ppm or so, and maintained at the ratio to within about +/−25% during the polymerization run. For instance, if the target ratio is 100 ppm, then maintaining the hydrogen:olefin monomer ratio substantially constant would entail maintaining the feed ratio between about 75 ppm and about 125 ppm. Further, the addition of comonomer (or comonomers) can be, and generally is, substantially constant throughout the polymerization run for a particular polymer grade.

However, in other aspects, it is contemplated that monomer, comonomer (or comonomers), and/or hydrogen can be periodically pulsed to the reactor, for instance, in a manner similar to that employed in U.S. Pat. No. 5,739,220 and U.S. Patent Publication No. 2004/0059070, the disclosures of which are incorporated herein by reference in their entirety.

The concentration of the reactants entering the polymerization reactor system can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers (e.g., ethylene/α-olefin copolymers, ethylene homopolymers, etc.) produced by any of the polymerization processes disclosed herein. Articles of manufacture can be formed from, and/or can comprise, the polymers produced in accordance with this invention.

Polymers and Articles

Olefin polymers encompassed herein can include any polymer produced from any olefin monomer and comonomer(s) described herein. For example, the olefin polymer can comprise an ethylene homopolymer, a propylene homopolymer, an ethylene copolymer (e.g., ethylene/α-olefin, ethylene/1-butene, ethylene/1-hexene, ethylene/1-octene, etc.), a propylene copolymer, an ethylene terpolymer, a propylene terpolymer, and the like, including combinations thereof. In one aspect, the olefin polymer can be an ethylene/1-butene copolymer, an ethylene/1-hexene copolymer, or an ethylene/1-octene copolymer, while in another aspect, the olefin polymer can be an ethylene/1-hexene copolymer.

If the resultant polymer produced in accordance with the present invention is, for example, an ethylene polymer, its properties can be characterized by various analytical techniques known and used in the polyolefin industry. Articles of manufacture can be formed from, and/or can comprise, the ethylene polymers of this invention, whose typical properties are provided below.

In particular aspects, and unexpectedly, the ethylene polymers disclosed herein often can have a low molecular weight and a high melt flow rate. Moreover, such polymers can be produced in an olefin polymerization process in which no hydrogen is added. An illustrative and non-limiting example of an ethylene polymer (e.g., an ethylene homopolymer or an ethylene/α-olefin copolymer, such as an ethylene/1-butene copolymer, an ethylene/1-hexene copolymer, or an ethylene/1-octene copolymer) consistent with aspects of this invention can have a melt index in a range from about 250 to about 2000 g/10 min (or from about 400 to about 1000 g/10 min, or greater than 500 g/10 min), and/or a density in a range from about 0.87 to about 0.96 g/cm³ (or from about 0.89 to about 0.93 g/cm³), and/or a Mw in a range from about 10,000 to about 25,000 g/mol (or from about 12,000 to about 23,000 g/mol), and/or an Mn in a range from about 3,000 to about 13,000 g/mol (or from about 4,500 to about 10,000 g/mol), and/or a ratio of Mw/Mn in a range from about 2 to about 3.5 (or from about 2 to about 2.5).

Another illustrative and non-limiting example of an ethylene polymer (e.g., an ethylene homopolymer or an ethylene/α-olefin copolymer, such as an ethylene/1-butene copolymer, an ethylene/1-hexene copolymer, or an ethylene/1-octene copolymer) consistent with aspects of this invention can have a melt index in a range from about 10 to about 200 g/10 min (or from about 20 to about 150 g/10 min), and/or a density in a range from about 0.87 to about 0.96 g/cm³ (or from about 0.89 to about 0.93 g/cm³), and/or a Mw in a range from about 27,000 to about 65,000 g/mol (or from about 30,000 to about 60,000 g/mol), and/or an Mn in a range from about 12,000 to about 35,000 g/mol (or from about 14,000 to about 30,000 g/mol), and/or a ratio of Mw/Mn in a range from about 2 to about 3.5 (or from about 2 to about 2.5).

These illustrative and non-limiting examples of ethylene polymers consistent with the present invention also can have any of the polymer properties listed below and in any combination.

The densities of ethylene-based polymers produced using the catalyst systems and polymerization processes described herein often range from about 0.87 to about 0.96 g/cm³. In one aspect of this invention, the density of the ethylene polymer can be in a range from about 0.93 to about 0.96, or from about 0.87 to about 0.94 g/cm³. Yet, in another aspect, the density can be in a range from about 0.88 to about 0.93 g/cm³, such as, for example, from about 0.89 to about 0.93 g/cm³, from about 0.895 to about 0.925 g/cm³, or from about 0.90 to about 0.92 g/cm³.

Suitable non-limiting ranges for the melt index (MI) of the ethylene polymer can include a MI greater than or equal to about 10, a MI greater than or equal to about 20, a MI greater than or equal to about 50, a MI greater than or equal to about 75, a MI greater than or equal to about 100, a MI greater than or equal to about 200, a MI greater than or equal to about 500, a MI in a range from about 25 to about 2000, a MI in a range from about 25 to about 1000, a MI in a range from about 250 to about 2000, a MI in a range from about 50 to about 1500, a MI in range from about 50 to about 1000, a MI in a range from about 75 to about 750, a MI in a range from about 400 to about 1000, a MI in a range from about 100 to about 1500, a MI in a range from about 150 to about 1000, a MI in a range from about 200 to about 1500, a MI in range from about 500 to about 1750, a MI in a range from about 200 to about 750, a MI in range from about 10 to about 250, a MI in a range from about 10 to about 200, a MI in a range from about 20 to about 250, or a MI in a range from about 20 to about 150 g/10 min, and the like.

The ethylene polymer, in some aspects, can have a narrow molecular weight distribution. For instance, the ethylene polymer can have a ratio of Mw/Mn of less than or equal to about 4, such as in a range from about 2 to about 3.5, from about 2 to about 3, from about 2 to about 2.8, or from about 2 to about 2.5. Additionally or alternatively, the ethylene polymer can have a unimodal molecular weight distribution. Additionally or alternatively, the ethylene polymer can have a ratio of Mz/Mw of less than or equal to about 3, such as in a range from about 1.5 to about 3, from about 1.6 to about 2.8, from about 1.6 to about 2.5, or from about 1.7 to about 2.7.

The ethylene polymer, in some aspects, can have a number-average molecular weight (Mn) in a range from about 3,000 to about 15,000, from about 3,000 to about 13,000, from about 3,000 to about 10,000, from about 4,000 to about 15,000, from about 4,000 to about 13,000, from about 4,000 to about 11,000, from about 4,500 to about 10,000, or from about 5,000 to about 9,000 g/mol. In other aspects, the ethylene polymer can have a number-average molecular weight (Mn) in a range from about 11,000 to about 40,000, from about 12,000 to about 35,000, from about 12,000 to about 30,000, from about 13,000 to about 35,000, from about 14,000 to about 30,000, from about 12,000 to about 28,000, or from about 14,000 to about 28,000 g/mol.

Additionally or alternatively, the ethylene polymer can have a weight-average molecular weight (Mw) in a range from about 10,000 to about 30,000, from about 10,000 to about 25,000, from about 10,000 to about 20,000, from about 10,000 to about 18,000, from about 11,000 to about 25,000, from about 11,000 to about 22,000, from about 12,000 to about 23,000, or from about 12,000 to about 18,000 g/mol. Yet, in other aspects, the ethylene polymer can have a weight-average molecular weight (Mw) in a range from about 25,000 to about 70,000, from about 27,000 to about 65,000, from about 27,000 to about 60,000, from about 27,000 to about 57,000, from about 30,000 to about 65,000, from about 30,000 to about 60,000, or from about 30,000 to about 58,000 g/mol.

Moreover, the illustrative polymer properties described herein can be achieved without the addition of hydrogen to the polymerization reactor system, e.g., the catalyst compositions and polymerization processes disclosed herein are capable of producing olefin polymers, with their respective polymer properties and characteristics, in the absence of added hydrogen.

Surprisingly, olefin polymers (e.g., ethylene polymers) produced via catalyst systems and polymerization processes using an aromatic bicyclic bridged metallocene compound can have a Mw less (e.g., at least 5% less, at least 10% less, or at least 20% less, and often up to 50-80% less) than that of an olefin polymer produced by a process using a catalyst system containing a metallocene compound with a cyclohexyl bridging group (or other structurally identical metallocene compound with a different bridging group). This comparison is conducted at the same polymerization conditions and with the same other catalyst system components (same amount of metallocene compound, same amount/type of co-catalyst, same amount/type of activator, same polymerization temperature, etc.). Hence, the only difference is the aromatic bicyclic bridging group on the metallocene compound, as compared to a metallocene compound with a cyclohexyl bridging group (or other bridging group).

Likewise, olefin polymers (e.g., ethylene polymers) produced via catalyst systems and polymerization processes using an aromatic bicyclic bridged metallocene compound can have a Mn less (e.g., at least 5% less, at least 10% less, or at least 20% less, and often up to 50-80% less) than that of an olefin polymer produced by a process using a catalyst system containing a metallocene compound with a cyclohexyl bridging group (or other structurally identical metallocene compound with a different bridging group). As above, this comparison is conducted at the same polymerization conditions and with the same other catalyst system components and, therefore, the only difference is the aromatic bicyclic bridging group on the metallocene compound, as compared to a metallocene compound with a cyclohexyl bridging group (or other bridging group).

Also surprisingly, olefin polymers (e.g., ethylene polymers) produced via catalyst systems and polymerization processes using a saturated bicyclic bridged metallocene compound can have a Mw greater (e.g., at least 10% greater, at least 20% greater, or at least 50% greater, and often up to 80-150% greater) than that of an olefin polymer produced by a process using a catalyst system containing a metallocene compound with a cyclohexyl bridging group (or other structurally identical metallocene compound with a different bridging group). This comparison is conducted at the same polymerization conditions and with the same other catalyst system components (same amount of metallocene compound, same amount/type of co-catalyst, same amount/type of activator, same polymerization temperature, etc.). Hence, the only difference is the saturated bicyclic bridging group on the metallocene compound, as compared to a metallocene compound with a cyclohexyl bridging group (or other bridging group).

Likewise, olefin polymers (e.g., ethylene polymers) produced via catalyst systems and polymerization processes using a saturated bicyclic bridged metallocene compound can have a Mn greater (e.g., at least 10% greater, at least 20% greater, or at least 50% greater, and often up to 80-150% greater) than that of an olefin polymer produced by a process using a catalyst system containing a metallocene compound with a cyclohexyl bridging group (or other structurally identical metallocene compound with a different bridging group). As above, this comparison is conducted at the same polymerization conditions and with the same other catalyst system components and, therefore, the only difference is the saturated bicyclic bridging group on the metallocene compound, as compared to a metallocene compound with a cyclohexyl bridging group (or other bridging group).

Polymers of ethylene, whether homopolymers, copolymers, and so forth, can be formed into various articles of manufacture. Articles which can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Also contemplated herein is a method for forming or preparing an article of manufacture that comprises a polymer produced by any of the polymerization processes disclosed herein. For instance, the method can comprise (i) contacting a catalyst composition with an olefin monomer and an optional olefin comonomer under polymerization conditions in a polymerization reactor system to produce an olefin polymer, wherein the catalyst composition can comprise a bicyclic bridged metallocene (e.g., having formula (B)), an activator (e.g., an activator-support comprising a solid oxide treated with an electron-withdrawing anion), and an optional co-catalyst (e.g., an organoaluminum compound); and (ii) forming an article of manufacture comprising the olefin polymer. The forming step can comprise blending, melt processing, extruding, molding, or thermoforming, and the like, including combinations thereof.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Melt index (MI, g/10 min) was determined in accordance with ASTM D1238 at 190° C. with a 2,160 gram weight.

Molecular weights and molecular weight distributions were obtained using a PL-GPC 220 (Polymer Labs, an Agilent Company) system equipped with a IR4 detector (Polymer Char, Spain) and three Styragel HMW-6E GPC columns (Waters, MA) running at 145° C. The flow rate of the mobile phase 1,2,4-trichlorobenzene (TCB) containing 0.5 g/L 2,6-di-t-butyl-4-methylphenol (BHT) was set at 1 mL/min, and polymer solution concentrations were in the range of 1.0-1.5 mg/mL, depending on the molecular weight. Sample preparation was conducted at 150° C. for nominally 4 hr with occasional and gentle agitation, before the solutions were transferred to sample vials for injection. An injection volume of about 200 μL was used. The integral calibration method was used to deduce molecular weights and molecular weight distributions using a Chevron Phillips Chemical Company's HDPE polyethylene resin, MARLEX® BHB5003, as the standard. The integral table of the standard was pre-determined in a separate experiment with SEC-MALS. Mp is the peak molecular weight, Mn is the number-average molecular weight, Mw is the weight-average molecular weight, and Mz is the z-average molecular weight.

Fluorided silica-coated alumina activator-supports were prepared as follows. Bohemite was obtained from W.R. Grace & Company under the designation "Alumina A" and having a surface area of about 300 m$^2$/g, a pore volume of about 1.3 mL/g, and an average particle size of about 100 microns. The alumina was first calcined in dry air at about 600° C. for approximately 6 hours, cooled to ambient temperature, and then contacted with tetraethylorthosilicate in isopropanol to equal 25 wt. % SiO$_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina was collected and stored under dry nitrogen, and was used without exposure to the atmosphere.

Example 1

Using F1 as the starting material, Ligand L1, Metallocene M1-(NEt$_2$)$_2$, and Metallocene M1-Cl$_2$ were synthesized (structures shown below; Et=ethyl). In a round-bottomed flask under an atmosphere of nitrogen, the fulvene derived from cyclopentadiene and tetralone (F1, 1.13 g, 5.81 mmol) was dissolved in diethyl ether and cooled in a dry ice/acetone bath to −78° C. Lithium indenyl (0.850 g, 6.96 mmol) was weighed into a second flask, dissolved in diethyl ether, and added to the fulvene solution via cannula dropwise while stirring. The reaction mixture was stirred and warmed to room temperature overnight. The resulting pink slurry was cooled in an ice bath and 1.5 mL of a saturated aqueous solution of ammonium chloride was added. The resulting yellow solution was extracted with diethyl ether, the combined organics were washed with water, dried over magnesium sulfate, and the volatiles removed on a rotary evaporator. Heptane was added to the resulting solid and the mixture was put in a freezer, causing a white solid to precipitate. The yellow liquid was decanted from this mixture to leave 1.19 g of Ligand L1 as a white solid (66% yield).

The isolated ligand L1 (0.271 g, 0.873 mmol) was weighed into a 100 mL 2-neck round-bottomed flask, dissolved in 30 mL of diethyl ether, and cooled in an ice water bath. Next, nBuLi (2.5 M in hexane, 0.73 mL, 1.825 mmol) was added dropwise to the flask, resulting in a pale yellow solution. The reaction mixture was stirred and warmed to room temperature overnight. Then, ZrCl$_2$(NEt$_2$)$_2$(thf)$_2$ (0.397 g, 0.881 mmol) was weighed into a second flask attached to a swivel frit filter, and 15 mL of pentane was added to the second flask, and the mixture was cooled in an ice water bath. The mixture of L1 and nBuLi was added dropwise via cannula to the second flask, resulting in a bright yellow mixture that was stirred and warmed to room temperature overnight. The volatiles from this mixture were removed in vacuo, the yellow residue was dissolved in toluene, and the mixture was filtered to remove LiCl. NMR analysis of the resulting crude yellow oil indicated formation of Metallocene M1-(NEt$_2$)$_2$ as a 1.37:1 mixture of diastereomers. FIG. 1 illustrates the $^1$H NMR (CD$_2$Cl$_2$, 300 MHz) spectra for the Metallocene M1-(NEt$_2$)$_2$ isomer mixture.

Figure 2:
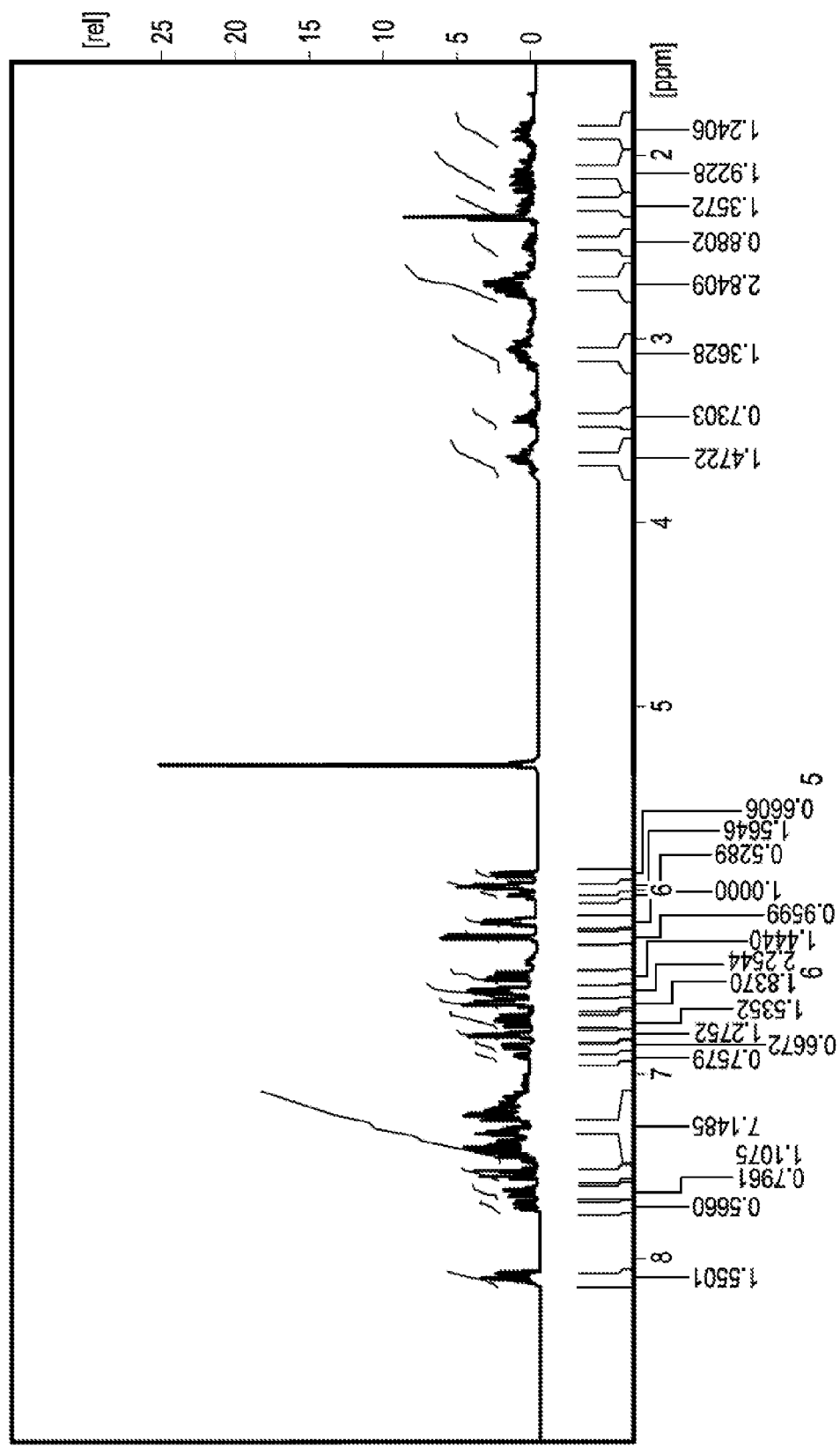
FIG. 2 presents a ¹H-NMR plot of the Metallocene M1-Cl₂ isomer mixture of Example 1.

A solution of M1-(NEt$_2$)$_2$ in toluene was cooled in an ice bath and chloro trimethylsilane (TMS-Cl, 1.65 mL, 7.87 mmol, 9.0 equiv.) was added dropwise. The reaction mixture was stirred and warmed to room temperature for three hours, then the volatile components were removed in vacuo. Pentane was added, resulting in the precipitation of a yellow solid. The solid was collected by filtration, washed multiple times with pentane, and dried in vacuo to give 0.17 g (41% yield) of Metallocene M1-Cl$_2$ as approximately a 1.8:1 mixture of configurational diastereomers (isomer structures shown below). FIG. 2 illustrates the $^1$H NMR (CD$_2$Cl$_2$, 300 MHz) spectra for the Metallocene M1-Cl$_2$ isomer mixture.

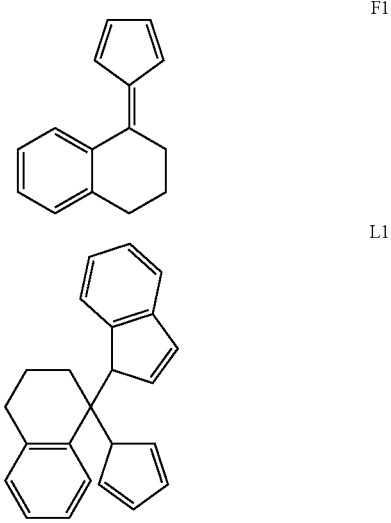

F1

L1

M1-(NEt₂)₂

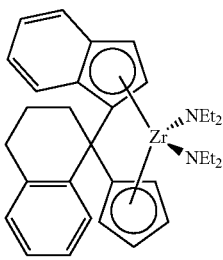

M1-Cl₂

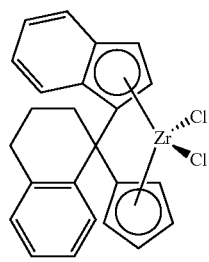

ISOMER MIXTURE:

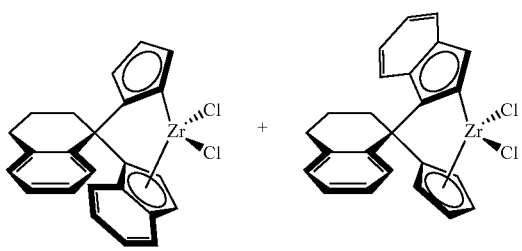

Example 2

Figure 3:
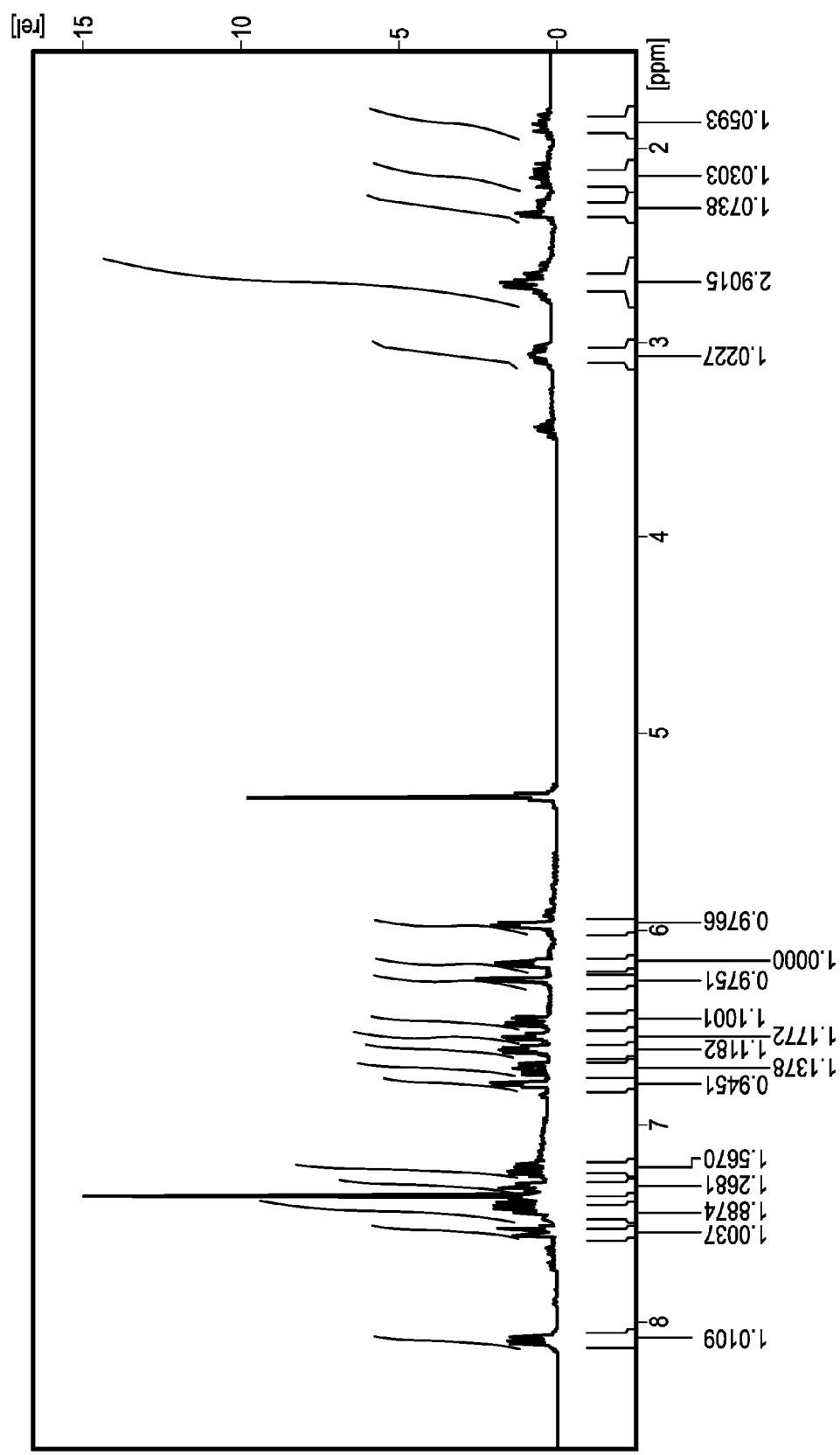
FIG. 3 presents a ¹H-NMR plot of the Metallocene M1-Cl₂ compound of Example 2.

Metallocene M1-Cl₂ was synthesized using a modified procedure in Example 2. The isolated ligand L1 (0.271 g, 0.873 mmol) was weighed into a 100 mL 2-neck round-bottomed flask, dissolved in 30 mL of diethyl ether, and cooled in an ice water bath. Next, nBuLi (2.5 M in hexane, 0.73 mL, 1.825 mmol) was added dropwise to the flask, resulting in a pale yellow solution. The reaction mixture was stirred and warmed to room temperature overnight. Then, ZrCl₂(NEt₂)₂(thf)₂ (0.396 g, 0.879 mmol) was weighed into a second flask attached to a swivel frit filter, and 15 mL of pentane was added to the second flask, and the mixture was cooled in an ice water bath. The mixture of L1 and nBuLi was added dropwise via cannula to the second flask, resulting in a bright yellow mixture that was stirred and warmed to room temperature overnight. Next, the resulting yellow mixture was cooled in an ice bath and chloro trimethylsilane (TMS-Cl, 1.65 mL, 7.87 mmol) was added dropwise. The reaction mixture was stirred and warmed to room temperature for six hours, then the volatile components were removed in vacuo. The resulting solids were dissolved in 10 mL of benzene and filtered. The solution was concentrated in vacuo, then pentane was added, which resulted in the precipitation of an orange solid. The solid was collected by filtration, washed multiple times with pentane, and dried in vacuo to give 0.174 g (43% yield) of Metallocene M1-Cl₂ as a single configurational diastereomer (structure shown below). FIG. 3 illustrates the ¹H NMR (CD₂Cl₂, 300 MHz) spectra for Metallocene M1-Cl₂: δ 8.09 (m, 1H), 7.54 (d, 1H), 7.42 (m, 2H), 7.32 (m, 1H), 7.20 (m, 1H), 6.79 (d, 1H), 6.69 (dd, 1H), 6.62 (dd, 1H), 6.55 (dd, 1H), 6.47 (d, 1H), 6.26 (d, 1H), 6.18 (dd, 1H), 5.98 (dd, 1H), 3.05 (m, 1H), 2.70 (m, 2H), 2.31 (m, 1H), 2.15 (m, 1H), 1.88 (m, 1H) ppm.

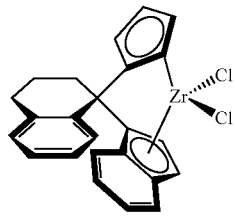

Example 3

Metallocene M1-Cl₂ was synthesized using a modified procedure in Example 3. The isolated ligand L1 (0.970 g, 2.67 mmol) was weighed into a 100 mL 2-neck round-bottomed flask, dissolved in 45 mL of diethyl ether, and cooled in an ice water bath. Next, nBuLi (2.5 M in hexane, 2.2 mL, 5.5 mmol) was added dropwise to the flask, resulting in a pale yellow solution. The reaction mixture was stirred and warmed to room temperature overnight. Then, ZrCl₂(NEt₂)₂(thf)₂ (1.10 g, 2.46 mmol) was weighed into a second flask attached to a swivel frit filter, and 15 mL of pentane was added to the second flask, and the mixture was cooled in an ice water bath. The mixture of L1 and nBuLi was added dropwise via cannula to the second flask, resulting in a bright yellow mixture that was stirred and warmed to room temperature overnight. The next day, the volatiles were removed, ~25 mL of toluene was added and the mixture was filtered to remove undissolved solids (LiCl, unreacted Zr, etc.). The solution was cooled in an ice bath and TMS-Cl (5.6 mL, 26.7 mmol, 10 equiv.) was added dropwise. The reaction mixture was stirred and heated to 55° C. for six hours, then left to stir at room temperature overnight. Next, the volatile components were removed in vacuo. Pentane was added, resulting in the precipitation of a yellow solid. The solid was collected by filtration, washed multiple times with pentane, and dried in vacuo to give 0.715 g (70% yield) of Metallocene M1-Cl₂ as approximately a 1.25:1 mixture of configurational diastereomers (isomer structures as in Example 1).

Example 4

Using F1 as the starting material, Ligand L2, Metallocene M2-(NEt₂)₂, and Metallocene M2-Cl₂ were synthesized (structures shown below; Et=ethyl). 1-(3-butenyl)indene (4.14 g, 24.3 mmol) was dissolved in pentane (60 mL) and cooled in an ice bath. Then, nBuLi (10 mL, 2.5 M, 25 mmol) was added dropwise by syringe, and the mixture was stirred and warmed to room temperature overnight. Next, the resulting white precipitate was collected by filtration and washed with pentane. The collected white solid was then dried under high vacuum on a Schlenk line, weighed out in a glove-box and stored in a freezer at −35° C. (3.84 g, 90% yield). The fulvene (F1, 2.3 g, 11.9 mmol) was added to a 250 mL round-bottomed flask, dissolved in Et₂O and cooled to −78° C. in a dry ice/acetone bath. In a second flask, lithium 1-(3-butenyl)indenyl (2.1 g, 11.9 mmol) was dissolved in Et₂O, and then added dropwise via cannula to the solution of F1. The reaction mixture was stirred and warmed to room temperature overnight. Next, the resulting red/ purple mixture was quenched by addition of a saturated aqueous solution of ammonium chloride. The mixture was then extracted with Et$_2$O, the combined organics washed with water, dried over magnesium sulfate, and the volatiles removed on a rotary evaporator to give a yellow oil. The crude material was then purified by column chromatography in 10% CH$_2$Cl$_2$/n-heptane to give the colorless oil (3.6 g, 83% yield) of Ligand L2.

In a 100 mL 2-neck round-bottomed flask, the isolated ligand L2 (0.97 g, 2.67 mmol) was dissolved in Et$_2$O (~20 mL) and cooled in an ice bath. Then, nBuLi (2.5 M in hexane, 2.2 mL, 5.5 mmol) was added dropwise via syringe, and the mixture was stirred and warmed to room temperature overnight. The reaction mixture was yellow with a brown oily precipitate. In a second flask, ZrCl$_2$(NEt$_2$)$_2$(thf)$_2$ (1.11 g, 2.46 mmol) was diluted in pentane and cooled in an ice bath. The mixture of lithiated L2 was added dropwise via cannula to the pentane slurry, and the mixture was stirred overnight to give a bright orange reaction mixture. The volatiles were removed in vacuo, and the remaining bright orange oil was analyzed by $^1$H NMR, which indicated formation of Metallocene M2-(NEt$_2$)$_2$ as a single configurational diastereomer. $^1$H NMR (CD$_2$Cl$_2$, 300 MHz): δ 8.26 (d, 1H), 7.39 (m, 2H), 7.31 (m, 1H), 7.18 (d, 1H), 6.72 (m, 1H), 6.59 (m, 2H), 6.31 (dd, 1H), 6.25 (m, 2H), 6.05 (dd, 1H), 5.97 (dd, 1H), 5.79 (m, 1H), 4.92 (m, 2H), 3.36 (q, 4H), 3.15 (m, 2H), 2.95 (m, 2H), 2.51 (q, 4H), 2.32 (m, 2H), 1.91 (m, 2H), 1.73 (m, 2H), 1.02 (t, 6H), 0.60 (t, 6H) ppm.

A solution of M2-(NEt$_2$)$_2$ (prepared as above, but with 1.55 mmol of L2) was dissolved in benzene, and the mixture was filtered to remove lithium chloride and any remaining insoluble zirconium species. TMS-Cl (2.9 mL, 22.8 mmol) was added by syringe to the resulting orange solution, the mixture was then heated to 60° C., and reacted overnight. Next, the reaction was cooled to room temperature, and the volatiles were reduced in vacuo to about 2-3 mL of a yellow/brown oil. Pentane was added with stirring, the solution cooled in an ice bath and filtered to give a yellow solid (329 mg, 40% yield). Using 2-D NMR techniques, detailed analysis of the resulting spectra indicated the formation of Metallocene M2-Cl$_2$ as the single configurational diastereomer structure shown below. $^1$H NMR (CD$_2$Cl$_2$, 300 MHz): δ 8.12 (1H, m), 7.45 (m, 1H). 7.45 (d, 1H), 7.41 (m, 1H), 7.39 (m, 1H), 7.20 (m, 1H), 6.68 (m, 1H), 6.60 (t, 2H), 6.42 (d, 1H), 6.18 (q, 1H), 5.92 (s, 1H), 5.85 (m, 1H), 5.80 (q, 1H), 4.96 (m, 2H), 2.95 (m, 1H), 2.93 (m, 2H), 2.69 (m, 2H), 2.40 (m, 2H), 2.26 (m, 1H), 2.10 (m, 1H), 1.86 (m, 1H) ppm.

L2

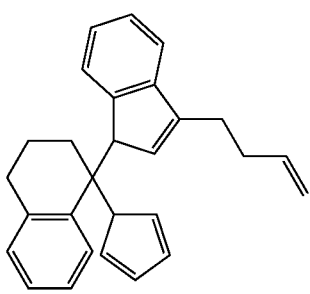

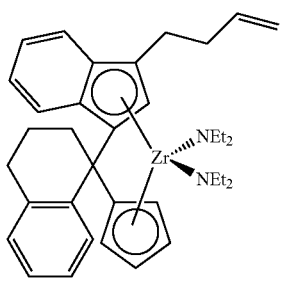

M2-(NEt$_2$)$_2$

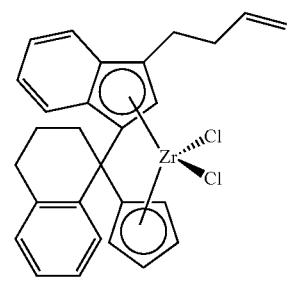

M2-Cl$_2$

ISOMER STRUCTURE:

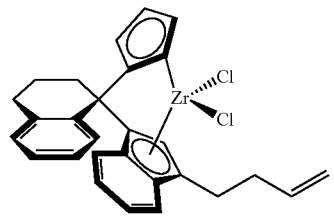

Example 5

Metallocene M2-Cl$_2$ was synthesized using a modified procedure in Example 5. The M2-(NEt$_2$)$_2$ was prepared as in Example 4 from 4.61 mmol of L2, and prior to filtration or removing volatiles, the solution of diethyl ether was split in two by removing half the solution to a second 100 mL round-bottomed flask. The mixture in the second flask was evaporated, then re-dissolved in THF. Both flasks were cooled in ice water and TMS-Cl (5.0 mL, 39.3 mmol) was added dropwise to each. The reaction in diethyl ether was stirred at room temperature overnight, while the reaction in THF was heated to 60° C. Then, both reactions were treated the same: the volatiles were removed in vacuo, benzene was added, the mixture was filtered, the solvent evaporated to about 10 mL, and pentane was added to precipitate a solid. The $^1$H NMR of the reaction performed in Et$_2$O showed no starting material or product; the $^1$H NMR of the reaction performed in THF indicated the formation of M2-Cl$_2$ the same single configurational diastereomer as in Example 4, along with polymerized THF.

Example 6

Using F1 as the starting material, Ligand L3 was synthesized (structure shown below). In a 100 mL 2-neck round-bottomed flask, fluorene (3.84 g, 22.6 mmol) was dissolved in 45 mL of diethyl ether and cooled in an ice water bath. nBuLi (2.5 M in hexane, 9.50 mL, 23.8 mmol) was added dropwise to the flask, and the reaction mixture was stirred and warmed to room temperature overnight. Then, the volatiles were removed in vacuo, and 40 mL of pentane was added. The precipitated solid was collected by filtration, washed several times with pentane, and dried in vacuo to give 3.92 g of lithium fluorenyl (77% yield).

In a clean 2-neck 100 mL round-bottomed flask, F1 (3.02 g, 15.5 mmol) was dissolved in diethyl ether and cooled to −78° C. in a dry ice/acetone bath. In a second flask, lithium fluorenyl (3.08 g, 17.78 mmol) was dissolved in diethyl ether and added to the cooled fulvene solution dropwise via cannula. The reaction mixture was stirred and warmed to room temperature overnight. Then, the resulting mixture was quenched by addition of a saturated aqueous solution of ammonium chloride. The mixture was then extracted with toluene, the combined organics washed with water, dried over magnesium sulfate, and the volatiles removed on a rotary evaporator. The resulting solid was washed several times with cold ether, and 4.1 g of a white solid (L3) was collected by filtration and appears as a mixture of isomers (73% yield). $^1$H NMR (CDCl$_3$, 300 MHz): δ 7.98 (t, 1H), 7.72 (dd, 2H), 7.34 (m, 2H), 7.25 (m, 3H), 7.11 (m, 3H), 6.86 (t, 1H), 6.78 (d, ~0.58H), 6.57 (m, 1H), 6.47 (m, 1H), 6.34 (s, ~0.58H), 5.88 (m, 1H), 4.93 (m, 1H), 3.13-3.38 (4 apparent singlets, Cp C$_{sp3}$—H, 2H), 2.61 (m, 1H), 2.37 (m, 1H), 1.70 (m, 2H), 1.40 (m, 1H), 1.01 (m, 1H) ppm.

In a 100 mL round-bottomed flask, L3 (1.86 g, 5.17 mmol) and 40 mL of diethyl ether were cooled in an ice water bath. nBuLi (10.5 mL, 18.12 mmol) was added dropwise, and the resulting orange reaction mixture was stirred and warmed to room temperature overnight. Then, the volatiles were reduced to a minimum on a vacuum line, pentane was added, and the mixture cooled in an ice water bath. A red solid was collected by filtration, washed several times with pentane, and dried in vacuo (2.19 g, 95% yield). $^1$H NMR analysis indicated the formation of the lithium dianion of L3 and one molecule of diethyl ether (Li$_2$L3). $^1$H NMR (d$_8$-thf, 300 MHz): δ 7.77 (d, 2H), 7.53 (dd, 1H), 6.90 (d, 1H), 6.83 (td, 1H), 6.73 (td, 1H), 6.39 (m, 2H), 6.15 (m, 4H), 5.70 (t, 2H), 5.61 (t, 2H), 3.38 (q, 4H, Et$_2$O), 3.09 (m, 1H), 2.89 (m, 1H), 2.70 (m, 1H), 1.80 (m, 2H), 1.12 (t, 6H, Et$_2$O) ppm.

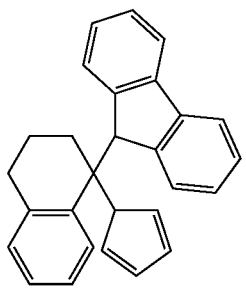

L3

Example 7

Using F1 as the starting material, Ligand L4 and Metallocene M4-(NEt$_2$)$_2$ were synthesized (structures shown below; Et=ethyl). In a 100 mL 2-neck round-bottomed flask, 2,7-di-tert-butylfluorene (1.72 g, 6.05 mmol) was dissolved in 25 mL of diethyl ether and cooled in an ice water bath. nBuLi (2.5 M in hexane, 2.54 mL, 6.35 mmol) was added dropwise, and the reaction mixture was stirred and warmed to room temperature overnight. Then, F1 (1.17 g, 6.02 mmol) was dissolved in diethyl ether in a second flask, and cooled to −78° C. in a dry ice/acetone bath. The solution of lithium 2,7-di-tert-butylfluorenyl was then added to the second flask dropwise via cannula. The reaction mixture was stirred and warmed to room temperature overnight. Next, the resulting mixture was quenched by addition of a saturated aqueous solution of ammonium chloride. The mixture was then extracted with dichloromethane (3×150 mL), the combined organics washed with water, dried over magnesium sulfate, and the volatiles removed on a rotary evaporator. The resulting solid was washed several times with cold ether, and 1.32 g of a white solid (L4) was collected by filtration (46% yield).

In a 100 mL round-bottomed flask, L4 (1.71 g, 3.62 mmol) was dissolved in 50 mL of diethyl ether and cooled in an ice water bath. nBuLi (7.25 mL, 18.12 mmol) was added dropwise, and the yellow reaction mixture was stirred and warmed to room temperature overnight. Then, the volatiles from the now orange solution were reduced to a minimum on a vacuum line, pentane was added, and the mixture cooled in an ice water bath. A red solid was collected by filtration, washed several times with pentane, and dried in vacuo (1.15 g, 51% yield). $^1$H NMR analysis indicated the formation of the lithium dianion of L4 (Li$_2$L4). $^1$H NMR (d$_8$-thf, 300 MHz): δ 7.68 (d, 2H), 7.65 (dd, 1H), 6.98 (d, 1H), 6.84 (td, 1H), 6.77 (td, 1H), 6.41 (dd, 2H), 6.29 (d, 2H), 5.85 (t, 2H), 5.71 (t, 2H), 3.08 (m, 1H), 2.87 (m, 2H), 2.66 (m, 1H), 1.97 (m, 2H), 1.15 (s, 18H) ppm.

In a glovebox, Li$_2$L4 (0.484 g, 0.998 mmol) and ZrCl$_2$(NEt$_2$)$_2$(thf)$_2$ (0.455 g, 1.01 mmol) were weighed into a 100 mL 2-neck round-bottomed flask. The flask was brought to a Schlenk line and cooled to −78° C. in a dry ice/acetone bath. Pentane (15 mL) was added to the flask, and then diethyl ether (25 mL) was added slowly to dissolve the reactants, resulting in a bright orange solution that was stirred and warmed to room temperature overnight. Then, the resulting slurry of yellow solid was placed under vacuum to remove volatiles, dissolved in benzene, and filtered. The benzene was then reduced to a minimal amount, and pentane was added to precipitate a yellow solid. The solid was collected by filtration, washed several times with pentane, and dried in vacuo to give 0.347 g (44% yield) of M4-(NEt$_2$)$_2$. $^1$H NMR (CD$_2$Cl$_2$, 300 MHz): δ 8.35 (d, 1H), 7.99 (d, 1H), 7.83 (d, 1H), 7.66 (s, 1H), 7.39 (t, 1H), 7.13 (m, 2H), 6.98 (d, 1H), 6.88 (d, 1H), 6.68 (s, 1H), 6.55 (s, 1H), 6.39 (m, 1H), 6.23 (m, 1H), 3.61 (m, 1H), 2.62 (m, 4H), 2.30 (m, 2H), 2.10 (m, 4H), 1.44 (s, 9H), 1.05 (s, 9H), 0.77 (t, 6H), 0.44 (t, 4H) ppm.

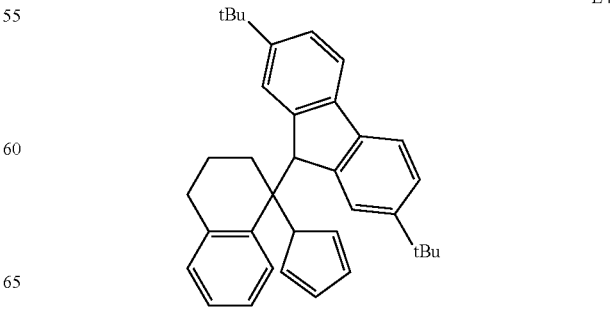

L4

M4-(NEt₂)₂

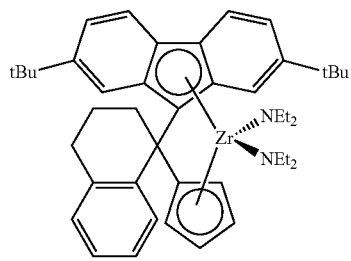

Examples 8-11

Using synthesis procedures analogous to those of Examples 1-7, but with F2 (containing an indane group) as the starting material, indane ligands L5, L6, L7, and L8 (Examples 8-11, with cyclopentadienyl, indenyl, and fluorenyl groups) were produced (tBu=tert-butyl):

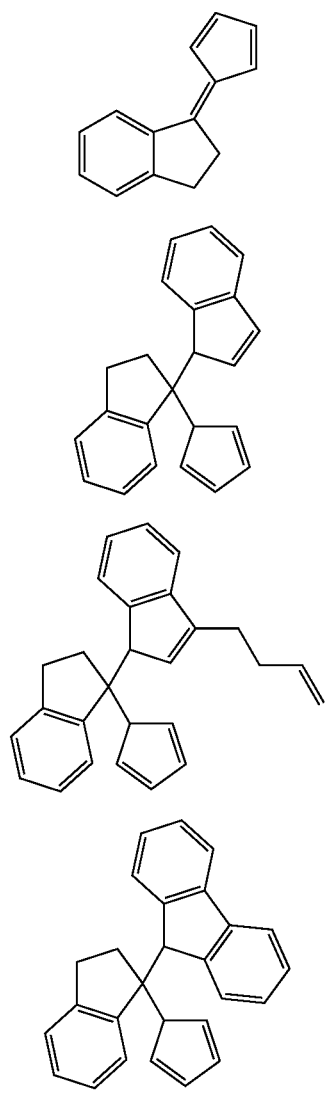

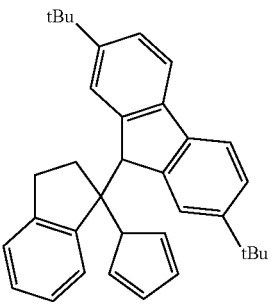

Constructive Examples 12-17

Using synthesis procedures analogous to those of Examples 1-7, the following bicyclic bridged metallocene compounds (with tetralin or decalin bridging groups) can be produced (tBu=tert-butyl; Me=methyl; Et=ethyl; R can be a hydrocarbyl substituent, such as a $C_1$ to $C_8$ alkyl group or a $C_3$ to $C_8$ alkenyl group; X can be a monoanionic ligand, such as a halide, a $C_1$ to $C_8$ hydrocarbyl group, or a $C_1$ to $C_8$ hydrocarbylaminyl group):

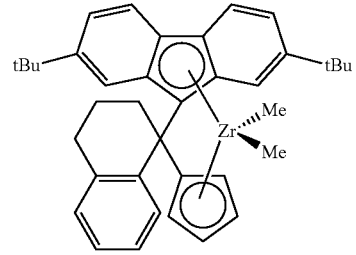

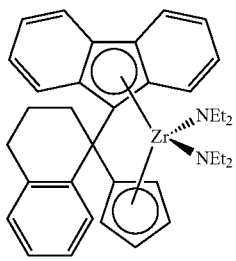 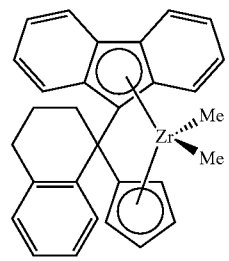

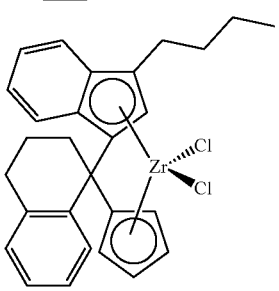 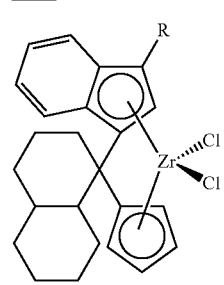

-continued

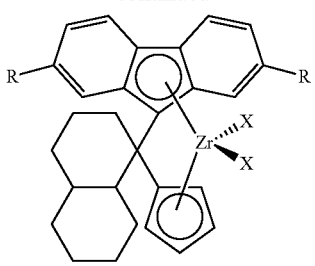

Examples 18-25

Examples 18-25 were produced using the following polymerization procedure. All polymerization runs were conducted in a one-gallon stainless steel reactor. Isobutane (1.2 L) was used in all runs. A metallocene solution of the desired bridged metallocene compound (structures for Metallocene A, Metallocene B, Metallocene C, and Metallocene D are shown below) was prepared at about 1 mg/mL in toluene. Approximately 200 mg of fluorided silica-coated alumina, 0.6 mmol of alkyl aluminum (triisobutylaluminum), and the metallocene solution (containing 2 mg of the metallocene compound) were added in that order through a charge port while slowly venting isobutane vapor. The charge port was closed and isobutane was added. The contents of the reactor were stirred and heated to the desired run temperature of about 80° C., and ethylene and 1-hexene (if used) were then introduced into the reactor. No hydrogen was added. Ethylene was fed on demand to maintain the target pressure of about 340 psig pressure for 30 min. The reactor was maintained at the desired temperature throughout the run by an automated heating-cooling system

A

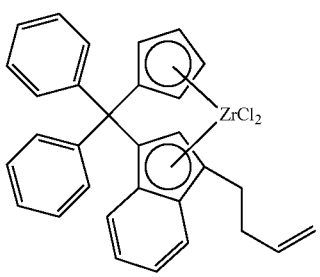

B

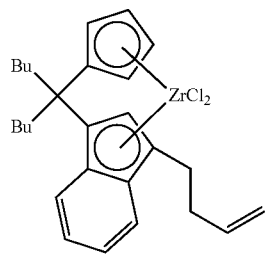

-continued

C

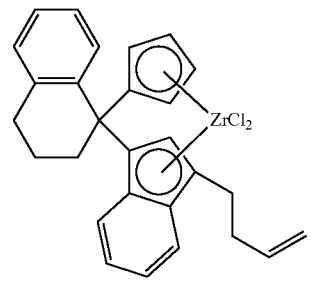

D

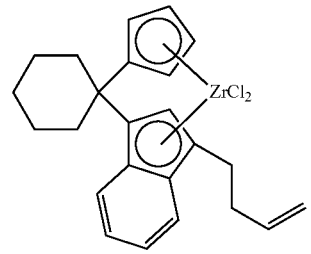

Figure 4:
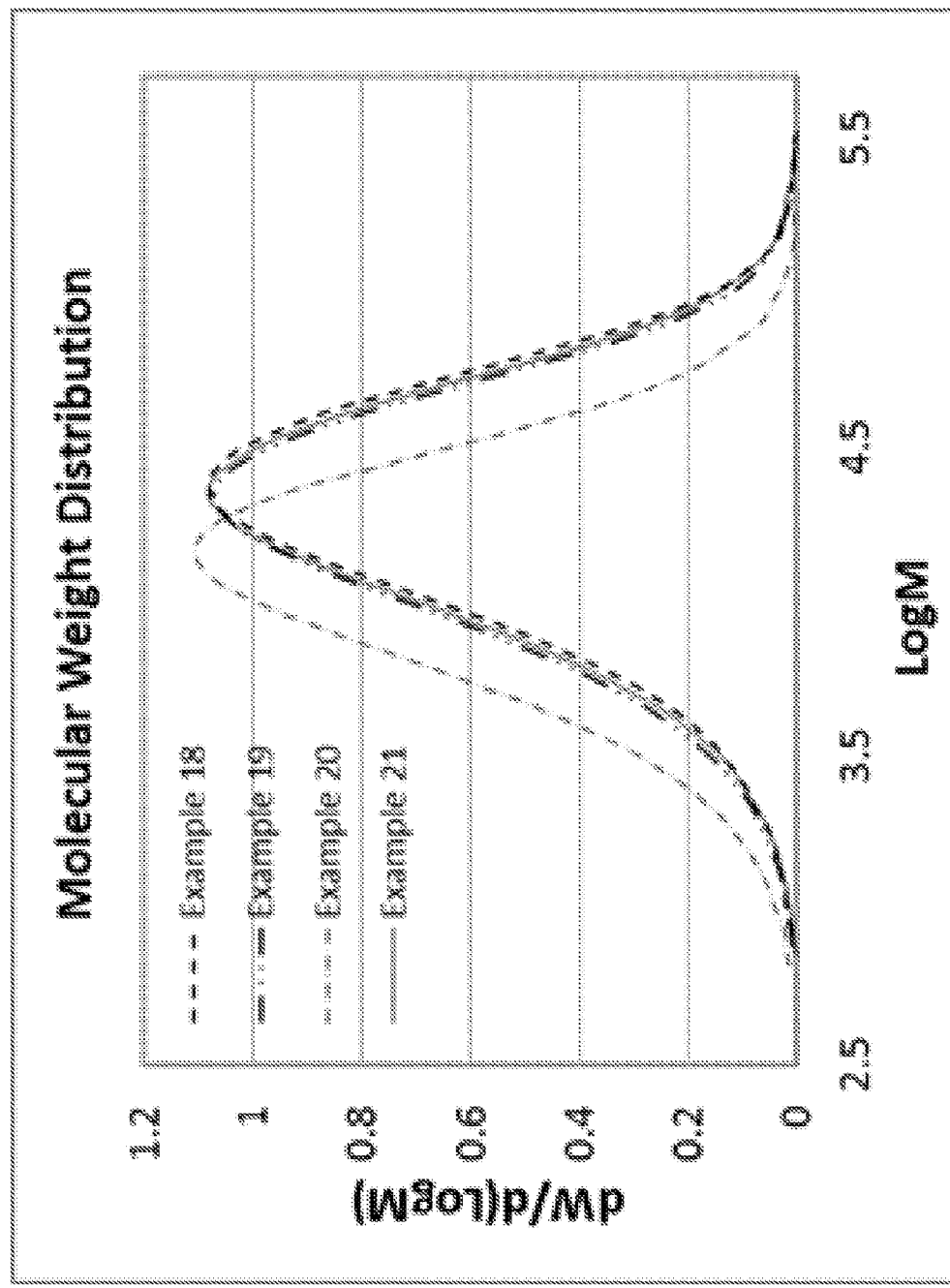
FIG. 4 presents a plot of the molecular weight distributions of the homopolymers of Examples 18-21, produced with catalyst systems containing different bridged metallocene compounds.
Figure 5:
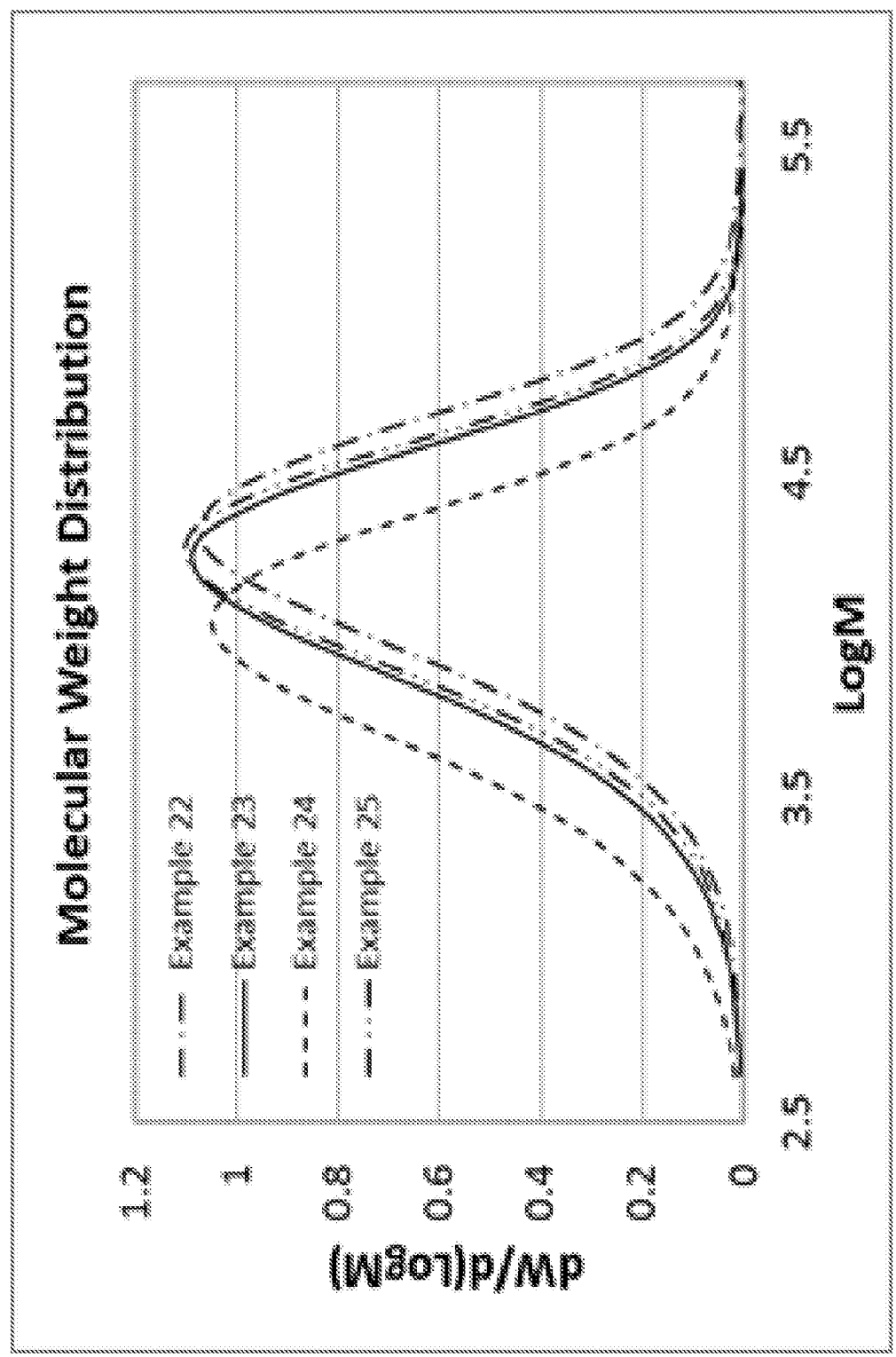
FIG. 5 presents a plot of the molecular weight distributions of the copolymers of Examples 22-25, produced with catalyst systems containing different bridged metallocene compounds.

Table I summarizes the metallocene compound, the amount of 1-hexene comonomer (if used), and the amount of polymer produced in Examples 18-25, as well as the respective Mn, Mw, Mz, Mw/Mn, and Mz/Mw for the resulting polymers of Examples 18-25. FIG. 4 and FIG. 5 illustrate the molecular weight distributions (amount of polymer versus logarithm of molecular weight) for the ethylene homopolymers of Examples 18-21 and the ethylene copolymers of Examples 22-25, respectively. The melt indices for the polymers of Examples 18-25 were over 100 g/10 min.

As shown in Table I and FIGS. 1-2, the polymers of Examples 20 and 24 (produced using an aromatic bicyclic bridged metallocene) had surprisingly low molecular weights. For homopolymers, the Mn and Mw values for Example 20 were, unexpectedly, over 30% less than those of the homopolymers of Examples 18-19 and 21. Likewise, for copolymers, the Mn and Mw values for Example 24 were, unexpectedly, over 30% less than those of the copolymers of Examples 22-23 and 25.

Example 26

Using F1 as the starting material, Ligand L9, Metallocene M5-(NEt$_2$)$_2$, and Metallocene M5-Cl$_2$ were synthesized (structures shown below; Et=ethyl). 1-butylindene (3.1 g, 18 mmol) was dissolved in diethyl ether (40 mL) and cooled in an ice bath. Then, nBuLi (7.3 mL, 2.5 M, 18.3 mmol) was added dropwise by syringe, and the mixture was stirred and warmed to room temperature overnight to produce a solution of lithium 1-butylindenyl. The fulvene (F1, 3.5 g, 18 mmol) was added to a 250 mL round-bottomed flask, dissolved in Et$_2$O, and cooled to −78° C. in a dry ice/acetone bath. The solution of lithium 1-(butyl)indenyl (2.1 g, 11.9 mmol) was then added dropwise via cannula to the solution of F1. The reaction mixture was stirred and warmed to room temperature overnight. Next, the resulting pink/purple mixture was quenched by addition of a saturated aqueous solution of ammonium chloride. The mixture was then extracted with Et$_2$O, the combined organics washed with water, dried over magnesium sulfate, and the volatiles removed on a rotary evaporator to give a yellow oil. The crude material was then purified by column chromatography in 10% CH$_2$Cl$_2$/heptane to give the colorless oil (3.36 g, 51% yield) of Ligand L9.

In a 100 mL 2-neck round-bottomed flask, the isolated ligand L9 (1.16 g, 3.16 mmol) was dissolved in Et$_2$O (~20 mL) and cooled in an ice bath. Then, nBuLi (2.5 M in hexane, 2.65 mL, 6.62 mmol) was added dropwise via syringe, and the mixture was stirred and warmed to room temperature overnight. The reaction mixture was a yellow slurry with a nearly colorless precipitate. In a second flask, ZrCl$_2$(NEt$_2$)$_2$(thf)$_2$ (1.43 g, 3.17 mmol) was diluted in ~10 mL pentane and cooled in an ice bath. The mixture of lithiated L9 was added dropwise via cannula to the pentane slurry, and the mixture was stirred overnight to give a bright orange reaction mixture. The volatiles were removed in vacuo, dissolved in benzene and filtered through Celite. The solvent was evaporated and the remaining bright orange oil was analyzed by $^1$H NMR, which indicated formation of Metallocene M5-(NEt$_2$)$_2$ as a single configurational diastereomer. $^1$H NMR (CD$_2$Cl$_2$, 300 MHz): δ 8.27 (d, 1H), 7.41 (m, 2H), 7.32 (m, 1H), 7.18 (d, 1H), 6.71 (m, 1H), 6.62 (m, 2H), 6.31 (dd, 1H), 6.25 (dd, 1H), 6.23 (s, 1H), 6.05 (dd, 1H), 5.97 (dd, 1H), 3.36 (m, 4H), 3.15 (m, 2H), 2.85-3.10 (m, 3H), 2.53 (q, 4H), 2.42 (m, 2H), 2.20 (m, 1H), 1.93 (m, 1H), 1.80 (m, 1H), 1.57 (m, 2H), 1.27 (m, 2H), 1.02 (t, 6H), 0.90 (t, 3H), 0.61 (t, 6H) ppm.

Figure 6:
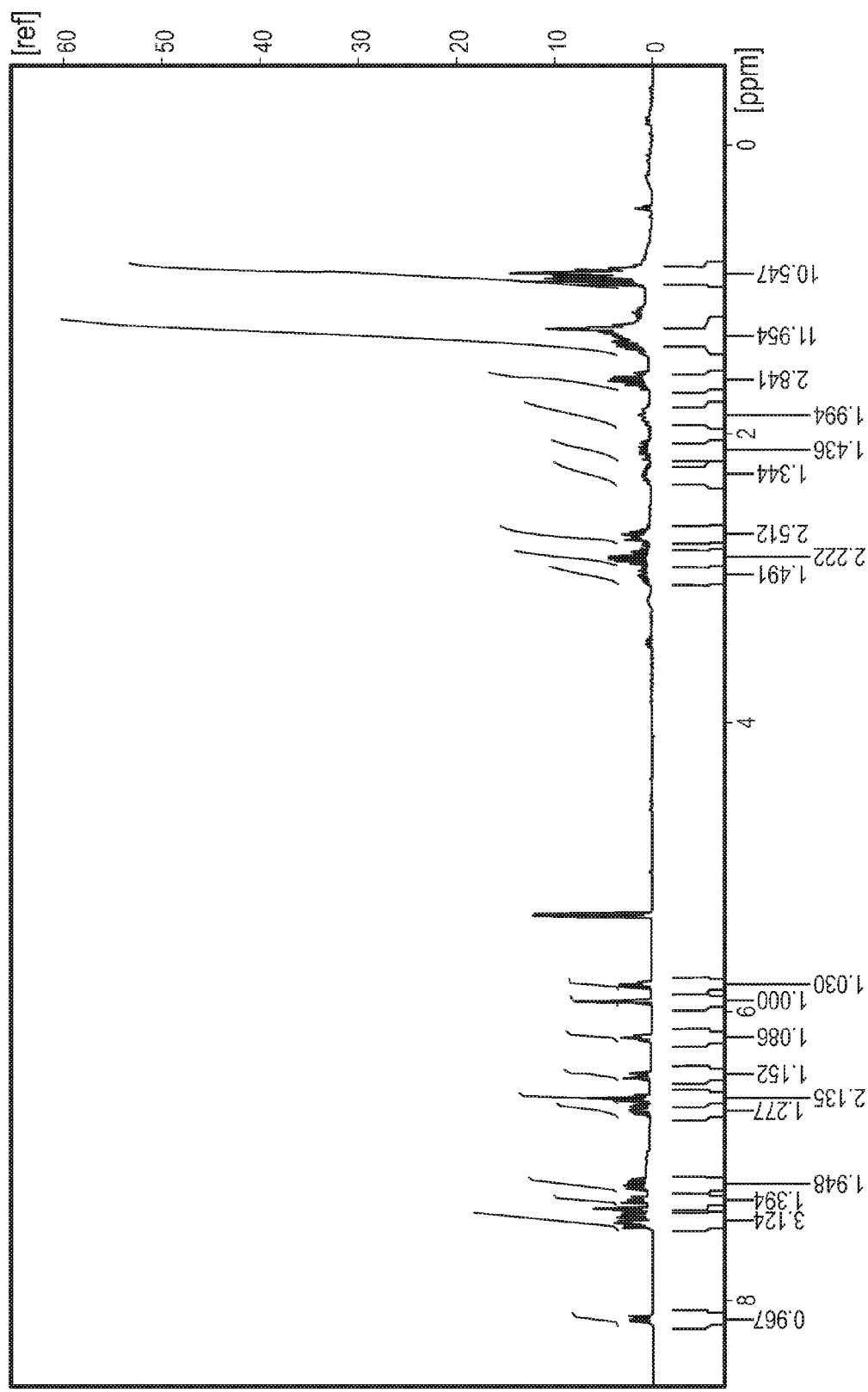
FIG. 6 presents a $^1$H-NMR plot of the Metallocene M5-Cl$_2$ compound of Example 26.

The M5-(NEt$_2$)$_2$ prepared above was dissolved in benzene, and TMS-Cl (4 mL, 31.5 mmol) was added by syringe to the solution, the mixture was then heated to 60° C., and reacted overnight. Next, the reaction was cooled to room temperature, and the volatiles were reduced in vacuo to about 2-3 mL of a yellow/brown oil. Pentane was added with stirring, the solution cooled in an ice bath and filtered to give a yellow solid (1.31 g, 79% yield). Using 2-D NMR techniques, detailed analysis of the resulting spectra indicated the formation of Metallocene M5-Cl$_2$ as the single configurational diastereomer structure shown below. FIG. 6 illustrates the 1H NMR (CD$_2$Cl$_2$, 300 MHz) spectra for Metallocene M5-Cl$_2$: δ 8.12 (1H, m), 7.47 (d, 1H). 7.43 (m, 1H), 7.39 (m, 1H), 7.30 (m, 1H), 7.19 (m, 1H), 6.67 (m, 1H), 6.60 (t, 1H), 6.60 (t, 1H), 6.44 (m, 1H), 6.17 (q, 1H), 5.92 (s, 1H), 5.81 (q, 1H), 2.98 (m, 1H), 2.86 (m, 2H), 2.70 (m, 2H), 2.28 (m, 1H), 2.18 (m, 1H), 1.87 (m, 1H), 1.64 (m, 2H), 1.37 (m, 2H), 0.94 (t, 3H) ppm.

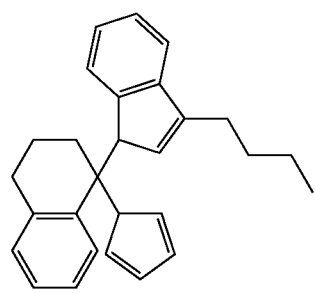

L9

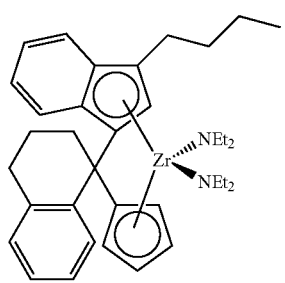

M5-(NEt$_2$)$_2$

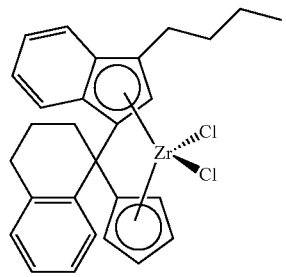

M5-Cl$_2$

ISOMER STRUCTURE:

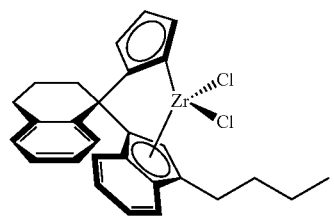

Example 27

The fulvene F3 was prepared by a manner analogous to F1 and F2. In a 100 mL 2-neck round-bottomed flask, trans-1-decalone (1.67 g, 10.9 mmol) was dissolved in 20 mL THF and cooled in an ice bath. To this solution, CpMgCl (1 M in THF, 13.6 mL, 13.6 mmol) was added dropwise over five minutes. The reaction mixture was allowed to stir 15 minutes, then the ice bath was removed, the reaction was refluxed for three hours, cooled to room temperature, and then stirred overnight. The next day, the reaction mixture was cooled in an ice bath and quenched with a saturated aqueous solution of ammonium chloride. The resulting mixture was diluted with 100 mL each of water and diethyl ether. Following extraction with diethyl ether, the combined organics were washed twice with 100 mL of water, dried over magnesium sulfate and the volatiles removed on a rotary evaporator to give a yellow oil. The crude material was purified by column chromatography in heptane to give F3 as a bright yellow oil (0.921 g, 42% Yield)

Using F3 as the starting material, Ligand L10, Metallocene M6-(NEt$_2$)$_2$, and Metallocene M6-Cl$_2$ were synthesized (structures shown below; Et=ethyl). 1-(3-butenyl)indene (1.22 g, 7.18 mmol) was dissolved in diethyl ether (25 mL) and cooled in an ice bath. Then, nBuLi (3.2 mL, 2.5 M, 8 mmol) was added dropwise by syringe, and the mixture was stirred and warmed to room temperature overnight. In a second round-bottomed flask under an atmosphere of nitrogen, the fulvene derived from F3 (1.34 g, 6.7 mmol) was dissolved in diethyl ether and cooled in a dry ice/acetone bath to −78° C. The solution of lithium 1-(3-butenyl)indenyl in diethyl ether was then added to the fulvene solution via cannula dropwise while stirring. The reaction mixture was stirred and warmed to room temperature overnight. The resulting red slurry was cooled in an ice bath and quenched with a saturated aqueous solution of ammonium chloride. The resulting yellow solution was extracted with diethyl ether, the combined organics were washed with water, dried over magnesium sulfate, and the volatiles removed on a rotary evaporator. The crude material was purified by column chromatography in 5% CH$_2$Cl$_2$/heptane to give L10 as a viscous yellow oil (1.68 g, 73% yield).

Figure 7:
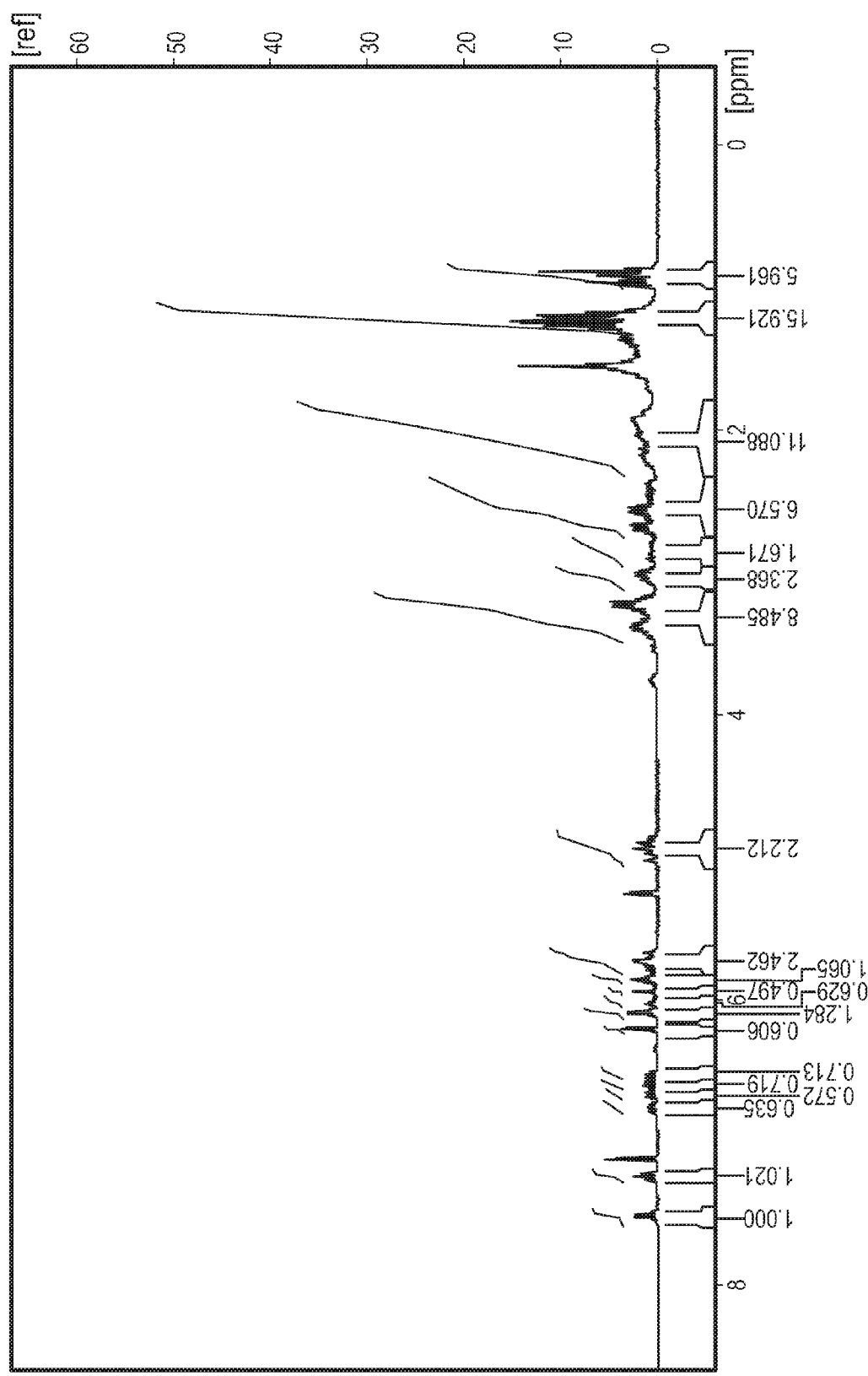
FIG. 7 presents a $^1$H-NMR plot of the Metallocene M6-(NEt$_2$)$_2$ isomer mixture of Example 27.

The isolated ligand L10 (1.68 g, 4.53 mmol) was weighed into a 100 mL 2-neck round-bottomed flask, dissolved in 25 mL of diethyl ether, and cooled in an ice water bath. Next, nBuLi (2.5 M in hexane, 3.8 mL, 9.5 mmol) was added dropwise to the flask, resulting in a pale yellow solution. The reaction mixture was stirred and warmed to room temperature overnight, giving a yellow slurry to which 20 mL THF was added in order to dissolve the precipitated solid. Then, ZrCl$_2$(NEt$_2$)$_2$(thf)$_2$ (2.14 g, 4.75 mmol) was weighed into a second flask, and 15 mL of pentane was added to the second flask, and the mixture was cooled in an ice water bath. The mixture of L10 and nBuLi was added dropwise via cannula to the second flask, resulting in a bright yellow mixture that was stirred and warmed to room temperature overnight. The volatiles from this mixture were removed in vacuo, the yellow residue was dissolved in benzene, and the mixture was filtered through Celite to remove undissolved solids (LiCl, Zr). NMR analysis of the resulting crude orange oil indicated formation of Metallocene M6-(NEt$_2$)$_2$ as a mixture of diastereomers. FIG. 7 illustrates the $^1$H NMR (CD$_2$Cl$_2$, 300 MHz) spectra for the Metallocene M6-(NEt$_2$)$_2$ isomer mixture.

Figure 8:
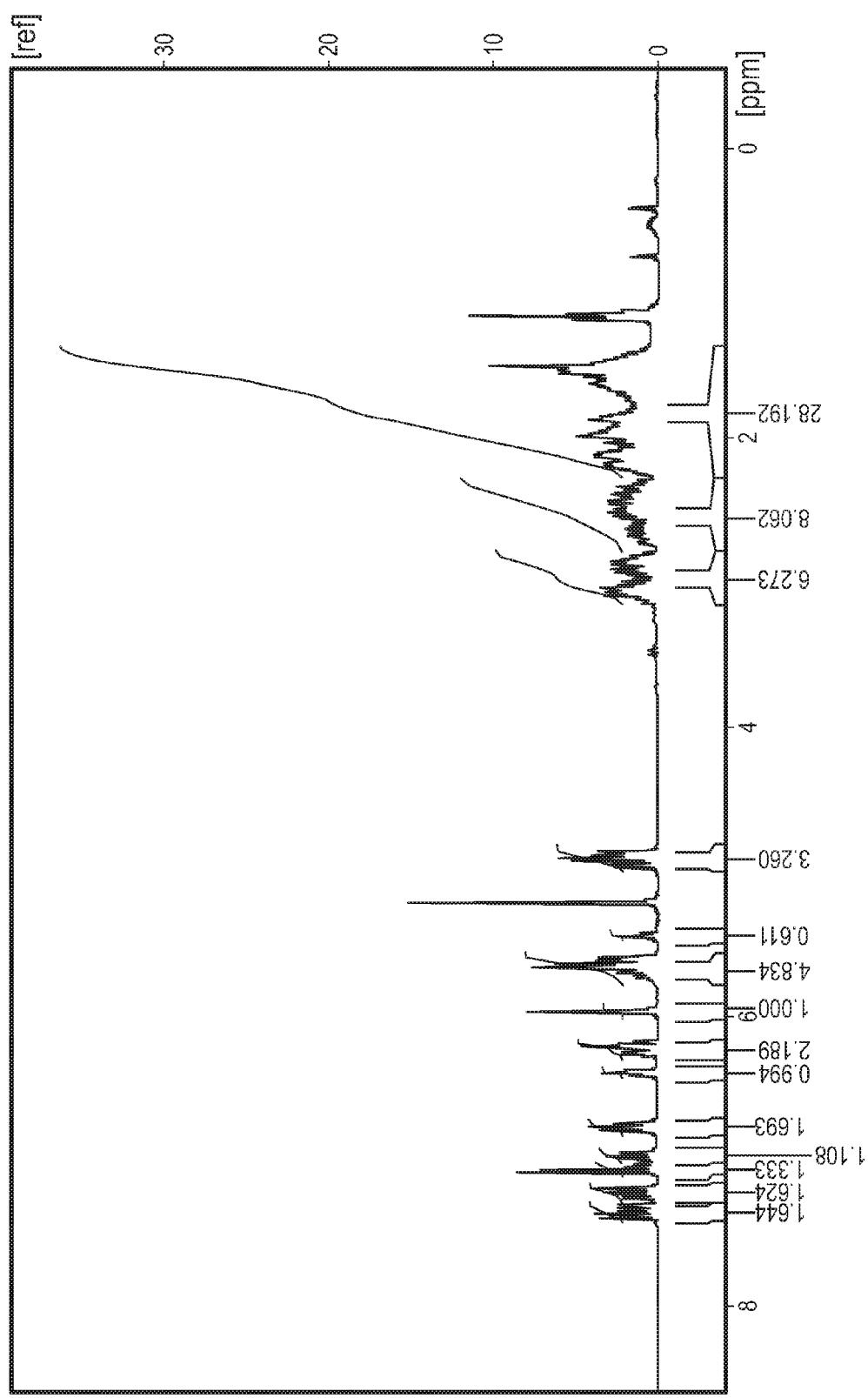
FIG. 8 presents a $^1$H-NMR plot of the Metallocene M6-Cl$_2$ isomer mixture of Example 27.

The collected M6-(NEt$_2$)$_2$ was dissolved in benzene, cooled in an ice bath and chloro trimethylsilane (TMS-Cl, 5.75 mL, 45.3 mmol, 10 equiv.) was added dropwise. The reaction mixture was heated to 60° C. for five hours then cooled to room temperature stirred overnight. The volatile components were removed in vacuo, and pentane was added, resulting in the precipitation of a yellow solid. The solid was collected by filtration, washed multiple times with pentane, and dried in vacuo to give 1.89 g (79% yield) of Metallocene M6-Cl$_2$ as approximately a 1.6:1 mixture of configurational diastereomers (isomer structures shown below). FIG. 8 illustrates the $^1$H NMR (CD$_2$Cl$_2$, 300 MHz) spectra for the Metallocene M6-Cl$_2$ isomer mixture.

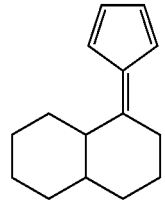

F3

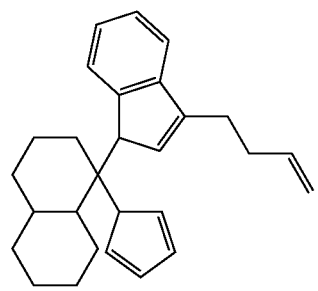

L10

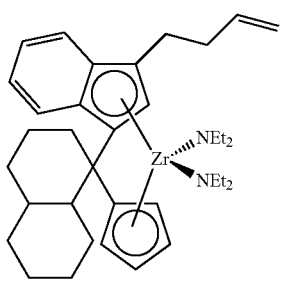

M6-(NEt$_2$)$_2$

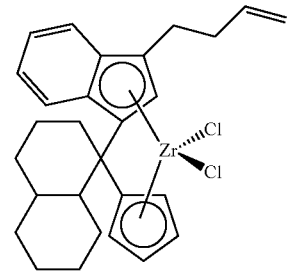

M6-Cl$_2$

ISOMER STRUCTURE:

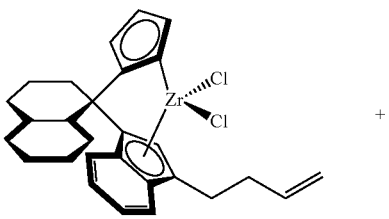

+

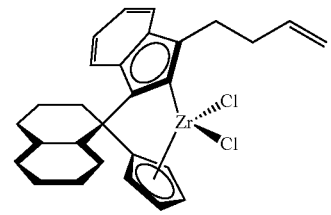

Example 28

Metallocene M6-Cl$_2$ was synthesized using a modified procedure in Example 28. The isolated ligand L10 (1.23 g, 3.32 mmol) was weighed into a 100 mL 2-neck round-bottomed flask, dissolved in 15 mL of diethyl ether, and cooled in an ice water bath. Next, nBuLi (2.5 M in hexane, 2.8 mL, 7 mmol) was added dropwise to the flask, resulting in a pale yellow solution. The reaction mixture was stirred and warmed to room temperature overnight, giving a yellow slurry to which 15 mL THF was added in order to dissolve the precipitated solid. Then, ZrCl$_2$(NEt$_2$)$_2$(thf)$_2$ (1.51 g, 3.34 mmol) was weighed into a second flask, and 10 mL of pentane was added to the second flask, and the mixture was cooled in an ice water bath. The mixture of L10 and nBuLi was added dropwise via cannula to the second flask, resulting in a bright yellow mixture that was stirred and warmed to room temperature overnight. The volatiles from this mixture were removed in vacuo, the yellow residue was dissolved in benzene, and the mixture was filtered through Celite to remove undissolved solids (LiCl, Zr). NMR analysis of the resulting crude orange oil indicated formation of Metallocene M6-(NEt$_2$)$_2$ as a mixture of diastereomers in a similar ratio to that observed above.

Figure 9:
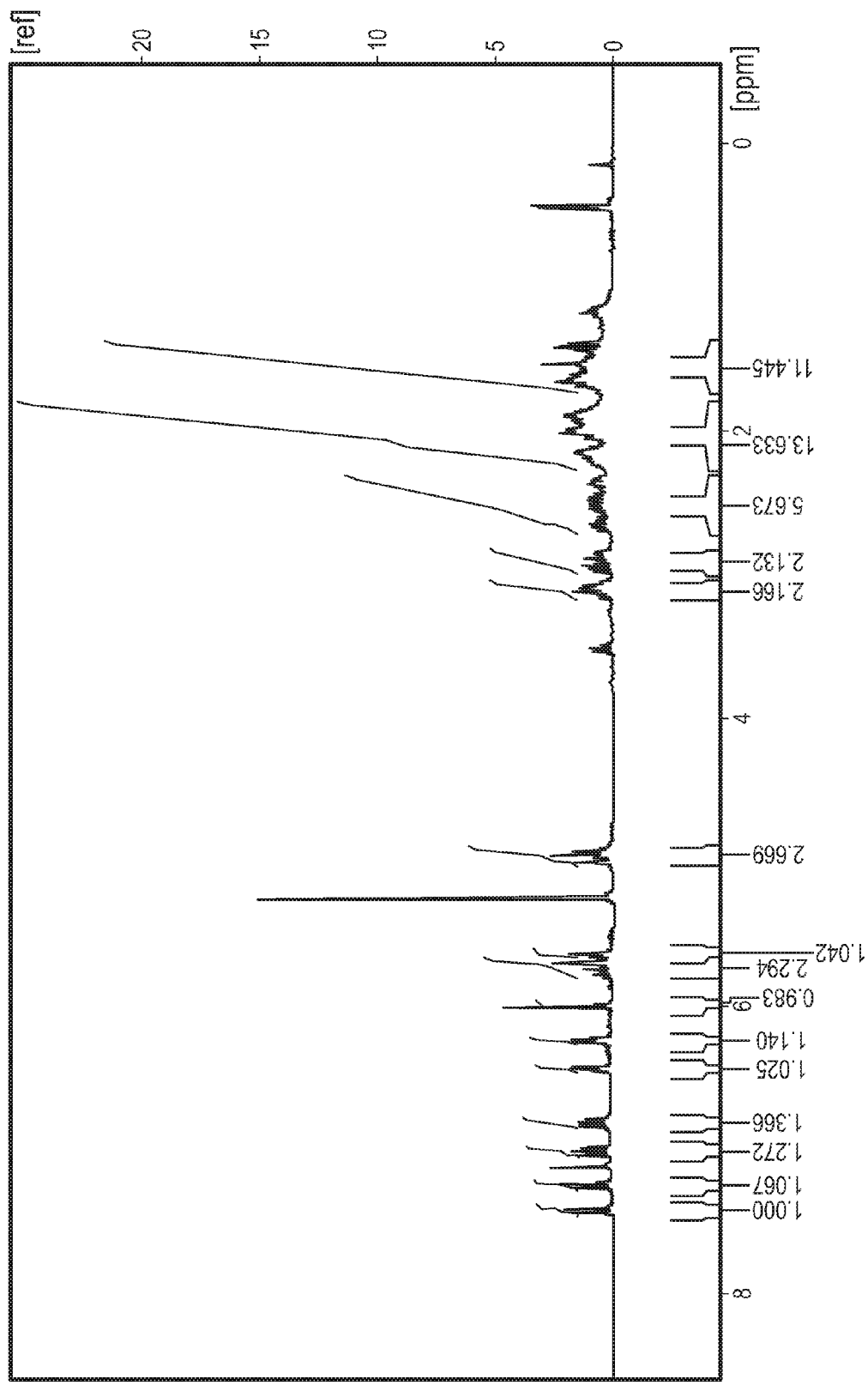
FIG. 9 presents a $^1$H-NMR plot of the Metallocene M6-Cl$_2$ compound of Example 28.

A sample of the freshly prepared M6-(NEt$_2$)$_2$ (1.5 mmol) was dissolved in 40 mL diethyl ether, transferred to a dry round-bottomed flask attached to a swivel frit filter. The solution was cooled in an ice bath, chloro trimethylsilane (TMS-Cl, 1.9 mL, 15 mmol, 10 equiv.) was added dropwise, and the reaction mixture was stirred and warmed to room temperature for six hours. The resulting yellow mixture was filtered to collect a yellow solid that was washed twice with a small amount of diethyl ether and dried in vacuo to yield 225 mg of M6-Cl$_2$ (28%) as a single configurational diastereomer. FIG. 9 illustrates the $^1$H NMR (CD$_2$Cl$_2$, 300 MHz) spectra for Metallocene M6-Cl$_2$: δ 7.68 (d, 1H), 7.49 (d, 1H), 7.24 (m, 1H), 7.01 (m, 1H), 6.61 (m, 1H), 6.40 (m, 1H), 6.14 (s, 1H), 5.82 (m, 1H), 5.80 (m, 1H), 5.74 (m, 1H), 4.99 (m, 2H), 2.97 (m, 2H), 2.74 (m, 2H), 2.15-2.52 (m, 6H), 1.32-2.03 (m, 10H) ppm.

Examples 29-34

Examples 29-34 were produced using the same polymerization procedure as in Examples 18-25, except that 220 mg of fluorided silica-coated alumina and 2.2 mg of the metallocene compound (structures for Metallocene A, Metallocene E, and Metallocene F are shown below) were used in the catalyst system, and the reaction time for each polymerization experiment ranged from 17 min to 30 min.

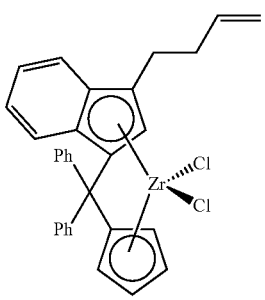

A

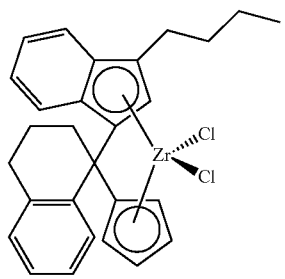

E

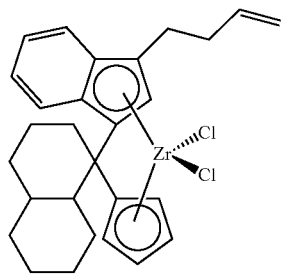

F

Table II summarizes the metallocene compound, the amount of 1-hexene comonomer (if used), the amount of polymer produced, the reaction time, and the catalyst activity (in grams of polymer per gram of metallocene per hour) for Examples 29-34, as well as the respective Mn, Mw, Mz, Mw/Mn, Mz/Mw, and melt index (MI, g/10 min) for the resulting ethylene polymers of Examples 29-34.

As shown in Table II, the polymers of Examples 31-32 (produced using an aromatic bicyclic bridged metallocene) had surprisingly low molecular weights. For the homopolymer, the Mn and Mw values for Example 31 were, unexpectedly, 25-35% less than those of the homopolymer of Example 29. Likewise, for copolymers, the Mn and Mw values for Example 32 were, unexpectedly, over 40% less than those of the copolymer of Example 30.

Also as shown in Table II, the polymers of Examples 33-34 (produced using a saturated bicyclic bridged metallocene) generally had low molecular weights, but were surprisingly high in view of Examples 29-32. For the homopolymer, the Mn and Mw values for Example 33 were, unexpectedly, over 80% greater than those of the homopolymer of Example 29. Likewise, for copolymers, the Mn and Mw values for Example 34 were, unexpectedly, about 30-65% greater than those of the copolymer of Example 30.

TABLE I

| | | Examples 18-25. | | | | | | |
|---|---|---|---|---|---|---|---|---|
| Example | Metallocene Compound | 1-hexene comonomer (g) | Polymer produced (g) | Mn/1000 (g/mol) | Mw/1000 (g/mol) | Mz/1000 (g/mol) | Mw/Mn | Mz/Mw |
| 18 | A | — | 300 | 12.8 | 28.0 | 50.2 | 2.2 | 1.8 |
| 19 | B | — | 322 | 11.8 | 26.0 | 47.6 | 2.2 | 1.8 |
| 20 | C | — | 287 | 8.2 | 17.0 | 30.5 | 2.1 | 1.8 |
| 21 | D | — | 256 | 12.5 | 27.3 | 50.3 | 2.2 | 1.8 |
| 22 | A | 22 | 317 | 11.3 | 26.8 | 77.0 | 2.4 | 2.8 |
| 23 | B | 20 | 287 | 8.9 | 19.8 | 36.1 | 2.2 | 1.8 |
| 24 | C | 20 | 145 | 5.7 | 13.5 | 29.2 | 2.4 | 2.2 |
| 25 | D | 21 | 267 | 9.7 | 21.3 | 39.4 | 2.2 | 1.8 |

TABLE II

Examples 29-34.

| Example | Metallocene Compound | 1-hexene comonomer (g) | Polymer produced (g) | Reaction Time (min) | Metallocene Activity (g/g/hr) | Mn/1000 (g/mol) | Mw/1000 (g/mol) | Mz/1000 (g/mol) | Mw/Mn | Mz/Mw | MI (g/10 min) |
|---|---|---|---|---|---|---|---|---|---|---|---|
| 29 | A | — | 194 | 17 | 306,000 | 13.7 | 29.1 | 52.9 | 2.1 | 1.8 | >200 |
| 30 | A | 21 | 204 | 20 | 280,000 | 9.6 | 26.4 | 159.5 | 2.8 | 6.1 | >200 |
| 31 | E | — | 87 | 30 | 79,000 | 9.1 | 21.2 | 47.3 | 2.3 | 2.2 | >500 |
| 32 | E | 20.5 | 58 | 30 | 53,000 | 5.6 | 12.9 | 31.3 | 2.3 | 2.4 | >500 |
| 33 | F | 0 | 196 | 19 | 280,000 | 24.7 | 54.3 | 99.5 | 2.2 | 1.8 | 23 |
| 34 | F | 20 | 208 | 24 | 241,000 | 15.9 | 34.9 | 61.6 | 2.2 | 1.8 | 109 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A ligand compound having the formula:

(A)

wherein:

$Cp^1$ and $Cp^2$ independently are a cyclopentadienyl, indenyl, or fluorenyl group, optionally substituted with any substituent (one or more) disclosed herein; and E is any bicyclic bridging group disclosed herein.

Aspect 2. A metallocene compound having the formula:

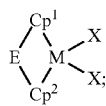

(B)

wherein:

M is Ti, Zr, or Hf; each X independently is any monoanionic ligand disclosed herein; $Cp^1$ and $Cp^2$ independently are a cyclopentadienyl, indenyl, or fluorenyl group, optionally substituted with any substituent (one or more) disclosed herein; and E is any bicyclic bridging group disclosed herein.

Aspect 3. The compound defined in aspect 1 or 2, wherein $Cp^1$ and $Cp^2$ are cyclopentadienyl groups.

Aspect 4. The compound defined in aspect 1 or 2, wherein $Cp^1$ and $Cp^2$ are indenyl groups.

Aspect 5. The compound defined in aspect 1 or 2, wherein $Cp^2$ is a cyclopentadienyl group, and $Cp^1$ is an indenyl group or a fluorenyl group.

Aspect 6. The compound defined in any one of aspects 1-5, wherein $Cp^1$ is unsubstituted.

Aspect 7. The compound defined in any one of aspects 1-5, wherein $Cp^1$ is substituted with any suitable substituent, any suitable number of substituents, and at any suitable position(s) that conforms to the rules of chemical valence.

Aspect 8. The compound defined in any one of aspects 1-5, wherein $Cp^1$ is substituted, and each substituent independently is any substituent disclosed herein, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 9. The compound defined in any one of aspects 1-5, wherein $Cp^1$ is substituted, and each substituent independently is H or a hydrocarbyl group having up to 18 carbon atoms.

Aspect 10. The compound defined in any one of aspects 1-5, wherein $Cp^1$ is substituted, and each substituent independently is an alkyl group (e.g., a $C_1$ to $C_8$ alkyl group) or an alkenyl group (e.g., a $C_3$ to $C_8$ terminal alkenyl group).

Aspect 11. The compound defined in any one of aspects 1-10, wherein $Cp^2$ is unsubstituted.

Aspect 12. The compound defined in any one of aspects 1-10, wherein $Cp^2$ is substituted with any suitable substituent, any suitable number of substituents, and at any suitable position(s) that conforms to the rules of chemical valence.

Aspect 13. The compound defined in any one of aspects 1-10, wherein $Cp^2$ is substituted, and each substituent independently is any substituent disclosed herein, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 14. The compound defined in any one of aspects 1-10, wherein $Cp^2$ is substituted, and each substituent independently is H or a hydrocarbyl group having up to 18 carbon atoms.

Aspect 15. The compound defined in any one of aspects 1-10, wherein $Cp^2$ is substituted, and each substituent independently is an alkyl group (e.g., a $C_1$ to $C_8$ alkyl group) or an alkenyl group (e.g., a $C_3$ to $C_8$ terminal alkenyl group).

Aspect 16. The compound defined in any one of aspects 1-15, wherein E is a $C_7$ to $C_{18}$ bicyclic bridging group, or a $C_7$ to $C_{10}$ bicyclic bridging group, optionally containing one or more heteroatoms.

Aspect 17. The compound defined in any one of aspects 1-16, wherein E is a saturated hydrocarbon group.

Aspect 18. The compound defined in any one of aspects 1-16, wherein E is an unsaturated hydrocarbon group.

Aspect 19. The compound defined in any one of aspects 1-16, wherein E is an aromatic hydrocarbon group.

Aspect 20. The compound defined in any one of aspects 1-16, wherein E is a tetralin group or a decalin group.

Aspect 21. The compound defined in any one of aspects 1-16, wherein E is a norbornane group, a norbornene group, or a norbornadiene group.

Aspect 22. The compound defined in any one of aspects 1-16, wherein E is an indane group, an indene group, or a dicyclopentadiene group.

Aspect 23. The compound defined in any one of aspects 2-22, wherein each X independently is H, $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $OBR^Z_2$, or $OSO_2R^Z$, wherein $R^Z$ is a $C_1$ to $C_{36}$ hydrocarbyl group.

Aspect 24. The compound defined in any one of aspects 2-22, wherein each X independently is any halide or $C_1$ to $C_{18}$ hydrocarbyl or hydrocarbylaminyl group disclosed herein.

Aspect 25. The composition defined in any one of aspects 2-22, wherein each X is Cl.

Aspect 26. The compound defined in any one of aspects 2-25, wherein M is Ti.

Aspect 27. The compound defined in any one of aspects 2-25, wherein M is Zr.

Aspect 28. The compound defined in any one of aspects 2-25, wherein M is Hf.

Aspect 29. A bicyclic-bridged metallocene compound containing two cyclopentadienyl groups, two indenyl groups, a cyclopentadienyl group and an indenyl group, or a cyclopentadienyl group and a fluorenyl group.

Aspect 30. A catalyst composition comprising the metallocene compound defined in any one of aspects 2-29, an activator, and an optional co-catalyst.

Aspect 31. The composition defined in aspect 30, wherein the activator comprises any activator disclosed herein.

Aspect 32. The composition defined in aspect 30 or 31, wherein the activator comprises an aluminoxane compound, an organoboron or organoborate compound, an ionizing ionic compound, or any combination thereof.

Aspect 33. The composition defined in any one of aspects 30-32, wherein the activator comprises an aluminoxane compound (e.g., a supported aluminoxane compound).

Aspect 34. The composition defined in any one of aspects 30-32, wherein the activator comprises an organoboron or organoborate compound.

Aspect 35. The composition defined in any one of aspects 30-32, wherein the activator comprises an ionizing ionic compound.

Aspect 36. The composition defined in aspect 30 or 31, wherein the activator comprises an activator-support, the activator-support comprising any solid oxide treated with any electron-withdrawing anion disclosed herein.

Aspect 37. The composition defined in aspect 36, wherein the solid oxide comprises any solid oxide disclosed herein, e.g., silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion comprises any electron-withdrawing anion disclosed herein, e.g., sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Aspect 38. The composition defined in aspect 36, wherein the activator-support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided-chlorided silica-coated alumina, fluorided silica-coated alumina, sulfated silica-coated alumina, phosphated silica-coated alumina, or any combination thereof.

Aspect 39. The composition defined in aspect 36, wherein the activator-support comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Aspect 40. The composition defined in aspect 36, wherein the activator-support comprises a fluorided solid oxide, a sulfated solid oxide, or any combination thereof.

Aspect 41. The composition defined in aspect 36, wherein the activator-support further comprises any metal or metal ion disclosed herein, e.g., zinc, nickel, vanadium, titanium, silver, copper, gallium, tin, tungsten, molybdenum, zirconium, or any combination thereof.

Aspect 42. The composition defined in any one of aspects 30-41, wherein the catalyst composition comprises a co-catalyst, e.g., any co-catalyst disclosed herein.

Aspect 43. The composition defined in any one of aspects 30-42, wherein the co-catalyst comprises an organoaluminum compound, an organozinc compound, an organomagnesium compound, an organolithium compound, or any combination thereof.

Aspect 44. The composition defined in any one of aspects 30-43, wherein the co-catalyst comprises an organoaluminum compound.

Aspect 45. The composition defined in aspect 44, wherein the organoaluminum compound comprises any organoaluminum compound disclosed herein, e.g., trimethylaluminum, triethylaluminum, triisobutylaluminum, etc., or combinations thereof.

Aspect 46. The composition defined in any one of aspects 36-45, wherein the catalyst composition is substantially free of aluminoxane compounds, organoboron or organoborate compounds, ionizing ionic compounds, or combinations thereof.

Aspect 47. The composition defined in any one of aspects 36-45, wherein the co-catalyst comprises an aluminoxane compound, an organoboron or organoborate compound, an ionizing ionic compound, an organoaluminum compound, an organozinc compound, an organomagnesium compound, an organolithium compound, or any combination thereof.

Aspect 48. The composition defined in any one of aspects 30-47, wherein the catalyst composition is produced by a process comprising contacting the metallocene compound and the activator.

Aspect 49. The composition defined in any one of aspects 30-47, wherein the catalyst composition is produced by a process comprising contacting, in any order, the metallocene compound, the activator, and the co-catalyst.

Aspect 50. The composition defined in any one of aspects 30-49, wherein a catalyst activity of the catalyst composition is in any range disclosed herein, e.g., greater than about 75,000 grams, greater than about 100,000 grams, greater than about 125,000 grams, greater than about 200,000 grams, etc., of ethylene polymer per gram of metallocene compound per hour, under slurry polymerization conditions, with a triisobutylaluminum co-catalyst, using isobutane as a diluent, and with a polymerization temperature of 80° C. and a reactor pressure of 340 psig.

Aspect 51. An olefin polymerization process, the process comprising contacting the catalyst composition defined in any one of aspects 30-50 with an olefin monomer and an optional olefin comonomer in a polymerization reactor system under polymerization conditions to produce an olefin polymer.

Aspect 52. The process defined in aspect 51, wherein the olefin monomer comprises any olefin monomer disclosed herein, e.g., any $C_2$-$C_{20}$ olefin.

Aspect 53. The process defined in aspect 51 or 52, wherein the olefin monomer and the optional olefin comonomer independently comprise a $C_2$-$C_{20}$ alpha-olefin.

Aspect 54. The process defined in any one of aspects 51-53, wherein the olefin monomer comprises ethylene.

Aspect 55. The process defined in any one of aspects 51-54, wherein the catalyst composition is contacted with ethylene and an olefin comonomer comprising a $C_3$-$C_{10}$ alpha-olefin.

Aspect 56. The process defined in any one of aspects 51-55, wherein the catalyst composition is contacted with ethylene and an olefin comonomer comprising 1-butene, 1-hexene, 1-octene, or a mixture thereof.

Aspect 57. The process defined in any one of aspects 51-53, wherein the olefin monomer comprises propylene.

Aspect 58. The process defined in any one of aspects 51-57, wherein the polymerization reactor system comprises a batch reactor, a slurry reactor, a gas-phase reactor, a solution reactor, a high pressure reactor, a tubular reactor, an autoclave reactor, or a combination thereof.

Aspect 59. The process defined in any one of aspects 51-58, wherein the polymerization reactor system comprises a slurry reactor, a gas-phase reactor, a solution reactor, or a combination thereof.

Aspect 60. The process defined in any one of aspects 51-59, wherein the polymerization reactor system comprises a loop slurry reactor.

Aspect 61. The process defined in any one of aspects 51-60, wherein the polymerization reactor system comprises a single reactor.

Aspect 62. The process defined in any one of aspects 51-60, wherein the polymerization reactor system comprises 2 reactors.

Aspect 63. The process defined in any one of aspects 51-60, wherein the polymerization reactor system comprises more than 2 reactors.

Aspect 64. The process defined in any one of aspects 51-63, wherein the olefin polymer comprises any olefin polymer disclosed herein.

Aspect 65. The process defined in any one of aspects 51-64, wherein the olefin polymer is an ethylene homopolymer, an ethylene/1-butene copolymer, an ethylene/1-hexene copolymer, or an ethylene/1-octene copolymer.

Aspect 66. The process defined in any one of aspects 51-64, wherein the olefin polymer is an ethylene/1-hexene copolymer.

Aspect 67. The process defined in any one of aspects 51-64, wherein the olefin polymer is a polypropylene homopolymer or a propylene-based copolymer.

Aspect 68. The process defined in any one of aspects 51-67, wherein the polymerization conditions comprise a polymerization reaction temperature in a range from about 60° C. to about 120° C. and a reaction pressure in a range from about 200 to about 1000 psig (about 1.4 to about 6.9 MPa).

Aspect 69. The process defined in any one of aspects 51-68, wherein the polymerization conditions are substantially constant, e.g., for a particular polymer grade.

Aspect 70. The process defined in any one of aspects 51-69, wherein no hydrogen is added to the polymerization reactor system.

Aspect 71. The process defined in any one of aspects 51-69, wherein hydrogen is added to the polymerization reactor system.

Aspect 72. The process defined in any one of aspects 51-71, wherein the olefin polymer has a density in any range disclosed herein, e.g., from about 0.87 to about 0.96, from about 0.87 to about 0.94, from about 0.88 to about 0.93, from about 0.89 to about 0.93, from about 0.93 to about 0.96, from about 0.90 to about 0.92 g/cm$^3$, etc.

Aspect 73. The process defined in any one of aspects 51-72, wherein the olefin polymer has a ratio of Mw/Mn in any range disclosed herein, e.g., from about 2 to about 3.5, from about 2 to about 3, from about 2 to about 2.8, from about 2 to about 2.5, etc.

Aspect 74. The process defined in any one of aspects 51-73, wherein the olefin polymer has a Mw in any range disclosed herein, e.g., from about 10,000 to about 25,000, from about 10,000 to about 20,000, from about 10,000 to about 18,000, from about 11,000 to about 25,000, from about 11,000 to about 22,000, from about 12,000 to about 23,000 g/mol, etc.

Aspect 75. The process defined in any one of aspects 51-73, wherein the olefin polymer has a Mw in any range disclosed herein, e.g., from about 25,000 to about 70,000, from about 27,000 to about 65,000, from about 27,000 to about 57,000, from about 30,000 to about 65,000, from about 30,000 to about 60,000, from about 30,000 to about 58,000 g/mol, etc.

Aspect 76. The process defined in any one of aspects 51-75, wherein the olefin polymer has a Mn in any range disclosed herein, e.g., from about 3,000 to about 13,000, from about 3,000 to about 10,000, from about 4,000 to about 13,000, from about 4,000 to about 11,000, from about 4,500 to about 10,000 g/mol, etc.

Aspect 77. The process defined in any one of aspects 51-75, wherein the olefin polymer has a Mn in any range disclosed herein, e.g., from about 11,000 to about 40,000, from about 12,000 to about 35,000, from about 13,000 to about 35,000, from about 14,000 to about 30,000, from about 12,000 to about 28,000 g/mol, etc.

Aspect 78. The process defined in any one of aspects 51-77, wherein the olefin polymer has a melt index (MI) in any range disclosed herein, e.g., greater than or equal to about 50, greater than or equal to about 200, greater than or equal to about 500, from about 250 to about 2000, from about 100 to about 1500, from about 400 to about 1000, from about 200 to about 1500 g/10 min, etc.

Aspect 79. The process defined in any one of aspects 51-77, wherein the olefin polymer has a melt index (MI) in any range disclosed herein, e.g., greater than or equal to about 10, greater than or equal to about 20, from about 10 to about 250, from about 10 to about 200, from about 20 to about 250, from about 20 to about 150 g/10 min, etc.

Aspect 80. The process defined in any one of aspects 51-79, wherein the olefin polymer has a unimodal molecular weight distribution.

Aspect 81. The process defined in any one of aspects 51-80, wherein the olefin polymer has a Mw less (e.g., at least 10% less, at least 20% less, etc.) than that of an olefin polymer produced by a process using a catalyst system containing an otherwise identical metallocene compound with a cyclohexyl bridging group, under the same polymerization conditions.

Aspect 82. The process defined in any one of aspects 51-80, wherein the olefin polymer has a Mn less (e.g., at least 10% less, at least 20% less, etc.) than that of an olefin polymer produced by a process using a catalyst system containing an otherwise identical metallocene compound with a cyclohexyl bridging group, under the same polymerization conditions.

Aspect 83. The process defined in any one of aspects 51-80, wherein the olefin polymer has a Mw greater (e.g., at least 10% greater, at least 20% greater, etc.) than that of an olefin polymer produced by a process using a catalyst system containing an otherwise identical metallocene compound with a cyclohexyl bridging group, under the same polymerization conditions.

Aspect 84. The process defined in any one of aspects 51-80, wherein the olefin polymer has a Mn greater (e.g., at least 10% greater, at least 20% greater, etc.) than that of an olefin polymer produced by a process using a catalyst system containing an otherwise identical metallocene compound with a cyclohexyl bridging group, under the same polymerization conditions.

Aspect 85. The process defined in any one of aspects 72-84, wherein no hydrogen is added to the polymerization reactor system, e.g., the catalyst compositions and polymerization processes disclosed herein are capable of producing olefin polymers, with their respective polymer properties and characteristics, in the absence of added hydrogen.

Aspect 86. An olefin polymer (e.g., an ethylene homopolymer or copolymer) produced by the olefin polymerization process defined in any one of aspects 51-85.

Aspect 87. An article comprising the olefin polymer defined in aspect 86.

Aspect 88. A method or forming or preparing an article of manufacture comprising an olefin polymer, the method comprising (i) performing the olefin polymerization process defined in any one of aspects 51-85 to produce an olefin polymer, and (ii) forming the article of manufacture comprising the olefin polymer, e.g., via any technique disclosed herein.

Aspect 89. The article defined in any one of aspects 87-88, wherein the article is an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, or a toy.

We claim:

1. An olefin polymerization process, the process comprising:
   contacting a catalyst composition with an olefin monomer and an optional olefin comonomer in a polymerization reactor system under polymerization conditions to produce an olefin polymer, wherein the catalyst composition comprises a metallocene compound, an activator, and an optional co-catalyst,
   wherein the metallocene compound has the formula:

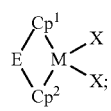

(B)

wherein:
   M is Ti, Zr, or Hf;
   each X independently is a monoanionic ligand;
   E is a saturated hydrocarbon bicyclic bridging group with a single carbon atom connected to $Cp^1$ and $Cp^2$; and
   $Cp^1$ and $Cp^2$ independently are a substituted or unsubstituted cyclopentadienyl, indenyl, or fluorenyl group.

2. The process of claim 1, wherein:
   M is Zr;
   each X independently is a halide, a $C_1$ to $C_{18}$ hydrocarbyl group, or a $C_1$ to $C_{18}$ hydrocarbylaminyl group;
   $Cp^1$ is a substituted or unsubstituted indenyl or fluorenyl group; and
   $Cp^2$ is a substituted or unsubstituted cyclopentadienyl group.

3. The process of claim 1, wherein at least one of $Cp^1$ and $Cp^2$ is unsubstituted.

4. The process of claim 1, wherein at least one of $Cp^1$ and $Cp^2$ has a substituent selected from H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

5. The process of claim 1, wherein at least one of $Cp^1$ and $Cp^2$ has a substituent selected from a $C_1$ to $C_8$ alkyl group or a $C_3$ to $C_8$ terminal alkenyl group.

6. The process of claim 1, wherein:
   E is a decalin group; and
   at least one of $Cp^1$ and $Cp^2$ has a $C_1$ to $C_{18}$ hydrocarbyl substituent.

7. The process of claim 6, wherein each X is Cl.

8. The process of claim 1, wherein the activator comprises an aluminoxane compound, an organoboron or organoborate compound, an ionizing ionic compound, or any combination thereof.

9. The process of claim 1, wherein the activator comprises an activator-support, the activator-support comprising a solid oxide treated with an electron-withdrawing anion.

10. The process of claim 1, wherein:
    the catalyst composition comprises an organoaluminum co-catalyst; and
    the activator comprises a fluorided solid oxide and/or a sulfated solid oxide.

11. The process of claim 1, wherein:
    the polymerization reactor system comprises a slurry reactor, gas-phase reactor, solution reactor, or a combination thereof; and
    the olefin monomer comprises ethylene, and the olefin comonomer comprises 1-butene, 1-hexene, 1-octene, or a mixture thereof.

12. The process of claim 1, wherein:
    the olefin polymer comprises an ethylene homopolymer or an ethylene/α-olefin copolymer; and
    the activator comprises an activator-support, an aluminoxane compound, an organoboron or organoborate compound, an ionizing ionic compound, or any combination thereof.

13. The process of claim 1, wherein the olefin polymer is an ethylene polymer characterized by:
    a melt index in a range from about 10 to about 200 g/10 min;
    a Mn in a range from about 12,000 to about 35,000 g/mol; and
    a Mw in a range from about 27,000 to about 65,000 g/mol.

14. The process of claim 13, wherein the process is conducted in the absence of added hydrogen, and the ethylene polymer is an ethylene homopolymer or an ethylene/α-olefin copolymer.

15. An olefin polymerization process, the process comprising:
    contacting a catalyst composition with an olefin monomer and an optional olefin comonomer in a polymerization reactor system under polymerization conditions to produce an olefin polymer, wherein the catalyst composition comprises a metallocene compound, an activator, and an optional co-catalyst, wherein the metallocene compound has the formula:

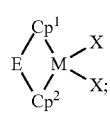
(B)

wherein:
M is Ti, Zr, or Hf;
each X independently is a monoanionic ligand;
E is an aromatic hydrocarbon bicyclic bridging group with a single carbon atom connected to $Cp^1$ and $Cp^2$; and
$Cp^1$ and $Cp^2$ independently are a substituted or unsubstituted cyclopentadienyl, indenyl, or fluorenyl group.

16. The process of claim 15, wherein:
M is Zr;
each X is Cl;
$Cp^1$ is a substituted or unsubstituted indenyl or fluorenyl group; and
$Cp^2$ is a substituted or unsubstituted cyclopentadienyl group.

17. The process of claim 16, wherein E is a tetralin group.

18. The process of claim 15, wherein:
the olefin polymer comprises an ethylene homopolymer or an ethylene/α-olefin copolymer; and
the activator comprises an aluminoxane compound, an organoboron or organoborate compound, an ionizing ionic compound, or any combination thereof.

19. The process of claim 15, wherein:
the catalyst composition comprises an organoaluminum co-catalyst;
the activator comprises a fluorided solid oxide and/or a sulfated solid oxide;
the polymerization reactor system comprises a slurry reactor, gas-phase reactor, solution reactor, or a combination thereof; and
the olefin monomer comprises ethylene, and the olefin comonomer comprises 1-butene, 1-hexene, 1-octene, or a mixture thereof.

20. The process of claim 15, wherein the olefin polymer is an ethylene polymer characterized by:
a melt index greater than 500 g/10 min;
a Mn in a range from about 3,000 to about 13,000 g/mol; and
a Mw in a range from about 10,000 to about 25,000 g/mol.

* * * * *